(12) United States Patent
Butler et al.

(10) Patent No.: US 6,793,621 B2
(45) Date of Patent: Sep. 21, 2004

(54) COLONIC OVERTUBE

(75) Inventors: John Butler, Blackrock (IE); Frank Bonadio, Bray (IE); Aoibheann Gill, Lanesboro (IE); Edmund Brennan, Monkstown Valley (IE)

(73) Assignee: Atropos Limited (IE)

( * ) Notice: Subject to any disclaimer, the term of this patent is extended or adjusted under 35 U.S.C. 154(b) by 57 days.

(21) Appl. No.: 10/092,528

(22) Filed: Mar. 8, 2002

(65) Prior Publication Data

US 2002/0147385 A1 Oct. 10, 2002

(30) Foreign Application Priority Data

Mar. 8, 2001 (IE) .............................. 20010220
Oct. 18, 2001 (IE) .............................. 20010916

(51) Int. Cl.⁷ .......................... A61B 1/00; A61M 25/00
(52) U.S. Cl. .................. 600/114; 604/526; 604/527
(58) Field of Search ............................ 600/114, 121, 600/101, 115; 604/524, 526, 527

(56) References Cited

U.S. PATENT DOCUMENTS

| | | | | |
|---|---|---|---|---|
| 3,778,170 A | * | 12/1973 | Howell et al. | 356/241.4 |
| 3,805,770 A | * | 4/1974 | Okada | 600/114 |
| 3,908,704 A | * | 9/1975 | Clement et al. | 138/121 |
| 3,913,565 A | * | 10/1975 | Kawahara | 600/585 |
| 4,332,242 A | * | 6/1982 | Chikama | 600/114 |
| 4,577,621 A | * | 3/1986 | Patel | 600/114 |
| 4,630,649 A | * | 12/1986 | Oku | 138/122 |
| 5,337,733 A | | 8/1994 | Bauerfeind et al. | |
| 5,454,364 A | * | 10/1995 | Kruger | 600/114 |
| 5,569,159 A | * | 10/1996 | Anderson et al. | 600/114 |
| 5,620,408 A | * | 4/1997 | Vennes et al. | 600/114 |
| 5,779,624 A | | 7/1998 | Chang | |
| 5,797,888 A | * | 8/1998 | Yoon | 604/530 |
| 5,941,815 A | | 8/1999 | Chang | |
| 6,016,848 A | * | 1/2000 | Egres, Jr. | 138/137 |
| 6,083,152 A | | 7/2000 | Strong | |
| 6,394,144 B1 | * | 5/2002 | Whitworth | 138/121 |
| 6,503,192 B1 | * | 1/2003 | Ouchi | 600/114 |
| 6,517,477 B1 | * | 2/2003 | Wendlandt | 600/114 |
| 6,554,820 B1 | * | 4/2003 | Wendlandt et al. | 604/527 |
| 6,605,063 B2 | * | 8/2003 | Bousquet | 604/175 |
| 6,607,010 B1 | * | 8/2003 | Kashy | 138/121 |

FOREIGN PATENT DOCUMENTS

| | | |
|---|---|---|
| DE | 41 13 265 A | 3/1992 |
| DE | 197 29 499 A | 1/1999 |
| GB | 2 306 111 A | 4/1997 |
| JP | 11-285533 | 10/1999 |
| JP | 2001-299684 | 10/2001 |

* cited by examiner

Primary Examiner—John P. Leubecker

(57) ABSTRACT

A colonic overtube 1 for maintaining a sigmoid colon in a straightened configuration has a proximal end 2 for location externally of a colon, and a distal end 3 for insertion into a colon. A colonoscope lumen 4 extends through the overtube 1 to facilitate passing the overtube 1 over a colonoscope. The overtube 1 has a convoluted corrugation 5 which extends along the entire length of the overtube 1 from the proximal end 2 to the distal end 3. The corrugated configuration of the overtube 1 provides the overtube 1 with laterally flexibility so that the overtube 1 may flex substantially without kinking during advancement of the overtube 1 through a colon. A flexible seal, in the form of a tubular silicone sheath 6 of film material, is provided at the distal end 3 of the overtube 1 for sealing between the overtube 1 and a colonoscope extending through the colonoscope lumen 4. The flexible nature of the seal 6 enables the seal 6 to adapt itself to the size of the colonoscope extending through the colonoscope lumen 4 to achieve a secure, effective seal between the overtube 1 and a colonoscope regardless of the colonoscope size.

71 Claims, 30 Drawing Sheets

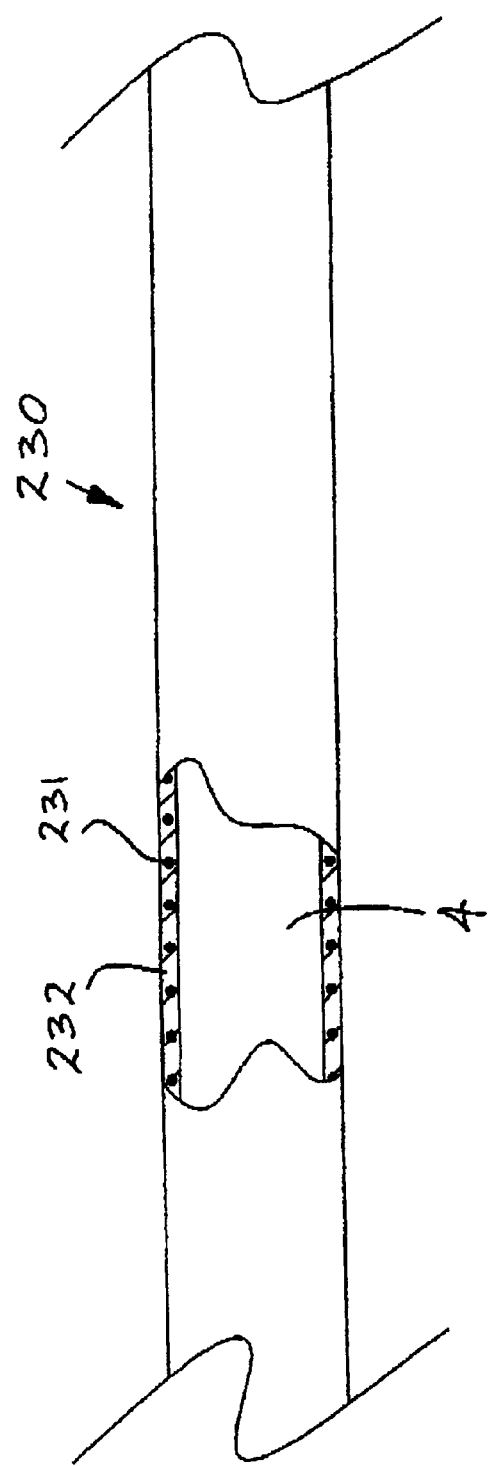

COLONIC OVERTUBE

INTRODUCTION

This invention relates to a colonic overtube for maintaining a section of a colon, such as a sigmoid colon, in a straightened configuration.

The lower gastrointestinal tract comprises the rectum, and the large intestine or colon. The colon, in a textbook arrangement of the human anatomy, extends upwards from the lower right quadrant, traverses the width of the body just below the diaphragm, travels downwards along the left side of the abdomen and then loops in an anterior retrograde manner before linking up with the rectum and the anus.

Even in such a textbook arrangement, the large intestine is difficult to cannulate with a colonoscope due to the flexible nature of the colonoscope and the floppy nature of the colon. This is even more difficult with the more realistic anatomies of actual people.

In some people, the sigmoid colon can be very long and is unfixed, except by its mesentery, and so can be extremely difficult to cannulate due to its predisposition to form loops when a colonoscope is pushed through it. Looping of the colonoscope within the sigmoid colon and transverse colon exacerbates the problems in traversing these areas.

Conventional colonoscopy procedures involve advancing a colonoscope through the floppy sigmoid colon to the proximal end of the descending colon. During advancement of the colonoscope through the sigmoid colon loops often form. It is difficult to then advance the colonoscope further, due to the looped nature of the sigmoid colon. Further pushing of the colonoscope simply increases the loops in the sigmoid colon without advancing the colonoscope into the descending colon.

The sigmoid colon is generally straightened by manipulation of the colonoscope. However advancing the colonoscope further, into the descending colon may cause the loops in the floppy sigmoid colon to reform.

It is known to use an overtube to prevent the reformation of loops by splinting the straightened sigmoid colon. The overtube is typically advanced over the colonoscope until the distal end of the overtube is at the proximal end of the descending colon. The overtube then maintains the sigmoid colon in the straightened configuration and prevents loops from reforming in the sigmoid colon during advancement of the colonoscope further, into the descending colon.

However, due to the potentially tortuous path through a colon, it is often difficult to advance an overtube over a colonoscope without kinking of the overtube occurring.

Furthermore, parts of the interior wall of a colon may become trapped between a colonoscope and an overtube during advancement of the overtube over the colonoscope. This may result in shearing off of the trapped part of the colon wall or puncturing of the colon wall.

In addition, in certain colonoscopy procedures, for example multiple polypectomy, it is necessary to insert and remove a colonoscope several times. This requires considerable skill on the part of the colonoscopist and takes a considerable length of time.

This invention is aimed at providing a colonic overtube which overcomes at least some of these problems.

STATEMENTS OF INVENTION

According to the invention there is provided a colonic overtube for maintaining a section of a colon in a straightened configuration, the overtube having a proximal end for location externally of a colon, a distal end for insertion into a colon, and a colonoscope lumen extending therethrough for passing the overtube over a colonoscope;

at least portion of the overtube being laterally flexible to facilitate flexing of the overtube substantially without kinking during advancement of the overtube through a colon.

The laterally flexible nature of the overtube of the invention enables the overtube to advance through a potentially tortuous path in a colon without kinking. This is particularly advantageous when the overtube is being advanced through a sharp bend in the colon, for example when advancing the overtube through the splenic or hepatic flexures or through parts of the sigmoid colon.

In one embodiment of the invention the laterally flexible portion of the overtube extends along the entire length of the overtube.

In another embodiment of the invention the overtube has more than one laterally flexible portion spaced along the overtube.

The laterally flexible portion may be provided by at least one corrugation. Preferably the corrugation extends along the overtube in a convoluted manner.

The corrugation may extend at least partially circumferentially around the overtube.

In a preferred embodiment of the invention the overtube comprises a plurality of corrugations. Ideally the corrugation is provided on an interior surface of the overtube. Most preferably an exterior surface of the overtube is smooth.

In another embodiment of the invention the overtube comprises a coating of a lubricious material.

The overtube may comprise a composite material. Preferably the overtube is of a layered construction. Ideally the overtube comprises a reinforcement means. The reinforcement means may be embedded in the overtube.

In one case the reinforcement means comprises a coil. In another embodiment the reinforcement means comprises a mesh. The reinforcement means may be of a braided construction.

Desirably the reinforcement means is of a metallic material.

In a preferred embodiment of the invention the overtube is of a material which is thermally stable in use. Ideally the overtube is of polytetrafluoroethylene.

In another preferred case the overtube is extendable between a shortened configuration and an elongated configuration for cannulating at least portion of a colon.

The overtube may comprise a flexible seal at the distal end for sealing between the overtube and a colonoscope extending through the colonoscope lumen.

In another aspect of the invention there is provided a colonic overtube for maintaining a section of a colon in a straightened configuration, the overtube having a proximal end for location externally of a colon, and a distal end for insertion into a colon, and a colonoscope lumen extending therethrough for passing the overtube over a colonoscope;

the overtube comprising a flexible seal at the distal end for sealing between the overtube and a colonoscope extending through the colonoscope lumen.

The colonic overtube of the invention has a flexible seal at the distal end of the overtube. The seal ensures that no parts of the colon wall become trapped between the overtube and the colonoscope during advancement of the overtube over the colonoscope. This arrangement prevents shearing off of the trapped part of the colon wall or puncturing of the colon wall.

In some colonoscopy procedures, air or some other gas is used to insufflate the colon, for example to blow a protruding piece of the wall of the colon laterally to clear a path for advancement of the overtube and/or the colonoscope further distally through the colon. A further advantage of the seal is that it prevents insufflation air from leaking proximally out of the colon between the colonoscope and overtube.

In addition the flexible nature of the seal enables the seal to adapt to the size of the colonoscope to achieve an effective seal between the overtube and the colonoscope for a variety of differently sized colonoscopes.

The seal preferably comprises a film material. The seal may comprise a sheath of film material. Ideally the seal comprises an inner sealing layer and an outer sealing layer around the inner sealing layer. Most preferably the seal is mounted to an exterior surface of the overtube. The seal may extend inwardly to seal between the overtube and a colonoscope extending through the colonoscope lumen. Desirably the seal extends distally of the distal end of the overtube.

According to another aspect of the invention there is provided a colonic overtube for maintaining a section of a colon in a straightened configuration, the overtube having a proximal end for location externally of a colon, a distal end for insertion into a colon, and a colonoscope lumen extending therethrough for passing the overtube over a colonoscope;

the overtube being of a material which is thermally stable in use.

Because the overtube is of a thermally stable material, the stiffness of the overtube may be chosen to be sufficiently flexible for ease of insertion into a colon, and to remain sufficiently stiff within the colon to maintain a section of the colon, such as the sigmoid colon, in a straightened configuration.

The overtube may be of polytetrafluoroethylene.

The overtube is preferably extendable between a shortened configuration and an elongated configuration for cannulating at least portion of a colon.

In a further aspect the invention provides a colonic overtube having a proximal end for location externally of a colon, a distal end for insertion into a colon, and a colonoscope lumen extending therethrough for passing the overtube over a colonoscope;

the overtube being extendable between a shortened configuration and an elongated configuration for cannulating at least portion of a colon.

The overtube according to the invention provides an ergonomic and easily workable means of cannulating the colon as far distally as the caecum, without requiring a long, awkward length of tubing externally of the colon.

In one embodiment of the invention in the shortened configuration at least portion of the overtube is retracted in a concertina-like manner.

In another embodiment of the invention the overtube comprises a plurality of overtube sections which are movable relative to one another to extend the overtube to the elongated configuration. The overtube sections may be releasably mountable to one another to extend the overtube to the elongated configuration.

In another case the overtube comprises an actuator to extend the overtube in situ to the elongated configuration. Preferably the actuator may be activated from externally of a colon. Ideally the actuator comprises a connector for extending from the overtube within a colon to a location externally of the colon. Most preferably the connector extends from the distal end of the overtube. The connector may be anchored to the overtube. Preferably the connector comprises a drawstring. Ideally the drawstring is configured to be looped through a working channel of a colonoscope to a location externally of a colonoscope.

In a further embodiment of the invention the overtube comprises a rounded tip at the distal end for atraumatic advancement of the overtube through a colon. The tip may be mounted to the overtube. Preferably the tip is mounted to an exterior surface of the overtube. Ideally the tip extends around the distal end of the overtube at least partially into the colonoscope lumen.

The rounded tip at the distal end of the overtube ensures that the overtube advances atraumatically through the colon. Any inadvertent contact between the distal end of the overtube and the interior wall of the colon will not result in damage or trauma to the colon.

In a preferred case the overtube comprises at least one exchange lumen for exchange of fluid and/or a medical device through the lumen. The overtube may comprise means to view a colon distally of the overtube, the viewing means being at least partially provided in the exchange lumen. The overtube may comprise means to insufflate a colon, the exchange lumen providing an insufflation channel. Preferably the overtube comprises means to flush a colon, the exchange lumen providing a flushing channel. Ideally the overtube comprises means to illuminate a colon, the illumination means being at least partially provided in the exchange lumen.

In a further embodiment of the invention the overtube comprises limiting means to prevent complete insertion of the overtube into a colon. The position of the limiting means on the overtube may be adjustable. Preferably the limiting means is releasably mounted to the overtube. Ideally the limiting means is threadably mounted to the overtube. Most preferably the limiting means comprises a flange.

In a preferred embodiment of the invention the overtube has a discontinuous interior surface for ease of passage of the overtube over a colonoscope. Ideally the overtube comprises one or more inwardly projecting elements on the interior surface for contacting a colonoscope. The projecting element may comprise a corrugation. In another case the projecting element comprises a protruding strip.

The projecting element may extend longitudinally along the overtube. The projecting element may extend at least partially circumferentially around the overtube. The projecting element may extend along the overtube in a convoluted manner.

In one embodiment the projecting element comprises a plurality of discrete protrusions.

In a preferred embodiment of the invention the colonic overtube may be used for maintaining a sigmoid colon in a straightened configuration.

In a further aspect of the invention there is provided a method of performing a colonoscopy procedure, the method comprising the steps of:

inserting a colonoscope into a colon and advancing the colonoscope through at least part of the colon;

straightening a section of the colon;

advancing a colonic overtube over the colonoscope to maintain the section of the colon in a straightened configuration;

advancing the colonoscope to a point distally of the straightened section of colon; and advancing the overtube over the colonoscope to a point distally of the straightened section of colon.

In one embodiment of the invention the method comprises the step of withdrawing the colonoscope from the colon while the overtube remains in place in the colon. The method may comprise the step of advancing a medical device through the overtube to access a point in the colon distally of the straightened section of colon.

Preferably the method comprises the step of mounting the overtube to the colonoscope before inserting the colonoscope into the colon.

In one case the overtube is advanced by extending the overtube from a shortened configuration to an elongated configuration. The overtube may be advanced by pushing the overtube from externally of the colon.

In a preferred case the section of colon being straightened is the sigmoid colon.

Ideally the overtube is advanced to a point distally of the descending colon.

The overtube provides a bridge between the fixed rectum and the fixed descending colon over the floppy sigmoid colon, thus preventing loops from reforming in the sigmoid colon. Furthermore, the overtube provides a bridge between the fixed descending colon and the fixed ascending colon over the floppy transverse colon, thus preventing loops from reforming in the transverse colon. Using the overtube of the invention advancement of a colonoscope through a colon as far as the caecum is easier and quicker, and causes less discomfort to a patient.

For an overtube to successfully splint a straightened sigmoid colon, its stiffness must be above the minimum threshold of stiffness required to prevent sigmoid loops from re-forming as the colonoscope is passed through the colonoscope lumen, and advanced further into the colon.

However it is also desirable that the overtube is not overly stiff, as insertion of the overtube becomes more difficult due to friction as the stiffness increases. This is because a "straightened" sigmoid colon is never perfectly straight. Consequently it is almost impossible to introduce a completely rigid overtube over the colonoscope. Some degree of compliance is required by the overtube.

While an overtube measured at room temperature may appear stiff enough to successfully splint a straightened sigmoid colon, this may no longer be the case at body temperature. Known overtube materials show a dramatic drop in stiffness between ambient room temperature and body temperature. In order for an overtube made from such materials to splint the sigmoid colon, it will have to be made overly rigid, so that it is still above the minimum threshold of stiffness required to prevent sigmoid loops from re-forming at body temperature. This excess rigidity causes serious insertion difficulties due to friction. Alternatively, if an overtube made from such materials was made less stiff, it may be easier to insert, but may not be stiff enough at body temperature to successfully splint the straightened sigmoid colon.

The overtube of the invention is configured to be relatively thermally stable. In this way the overtube at room temperature (insertion temperature) is selected to be sufficiently compliant or floppy to be easily inserted into a colon over a colonoscope. There is then a minimal drop in stiffness between ambient room temperature and body temperature compared to other materials, so that at body temperature the overtube is above the minimum threshold of stiffness required to prevent sigmoid loops from reforming.

Two other features of the overtube aid the insertion process: (a) corrugations, which minimise frictional contact with the scope; (b) extremely low friction PTFE material used in its construction.

BRIEF DESCRIPTION OF THE DRAWINGS

The invention will be more clearly understood from the following description of some embodiments thereof, given by way of example only, with reference to the accompanying drawings, in which:

FIG. 33 is a partially cross-sectional, side view of another overtube according to the invention.

DETAILED DESCRIPTION

Figure 1:
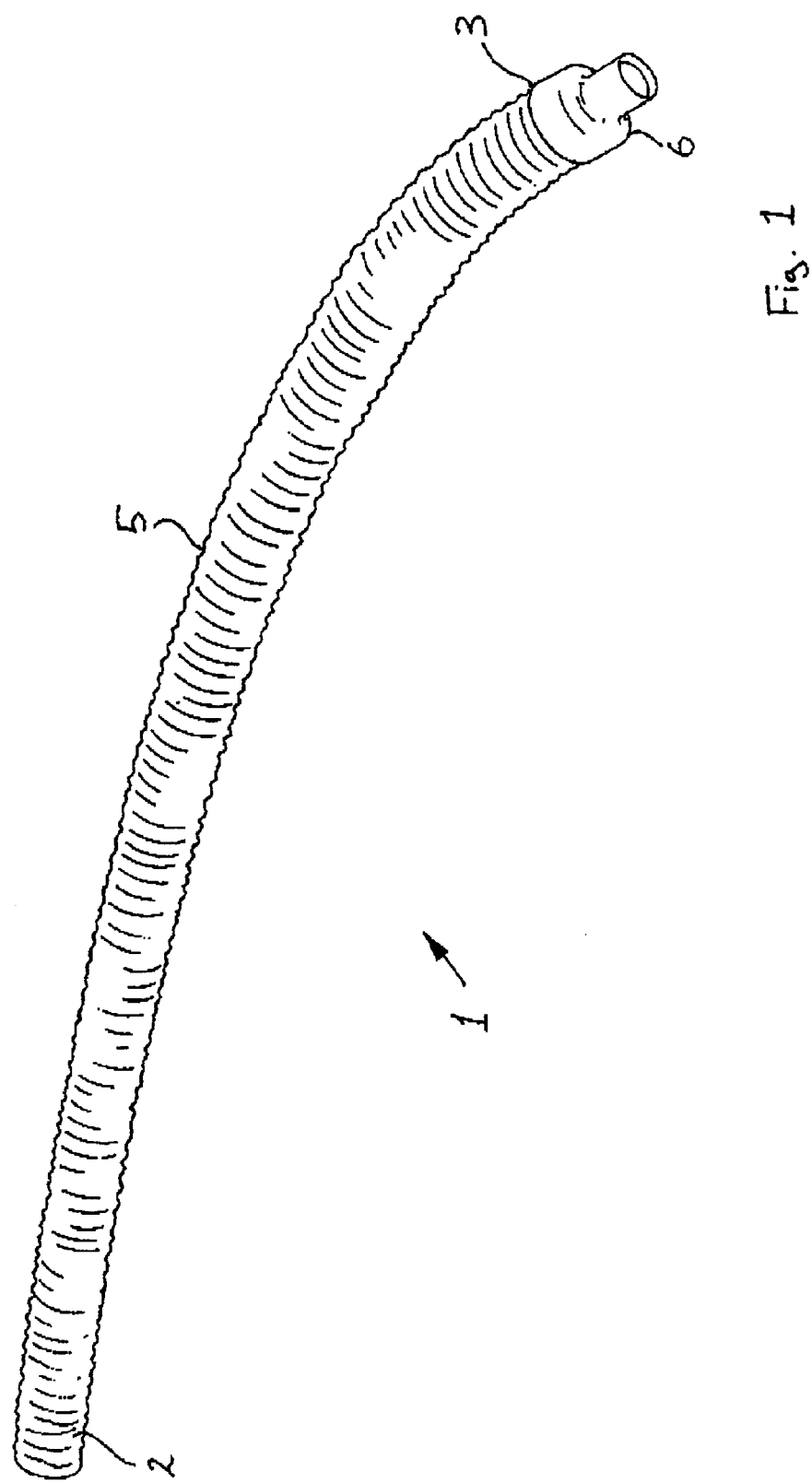
FIG. 1 is a perspective view of a colonic overtube according to the invention.

Referring to the drawings and initially to FIGS. 1 to 17 thereof, there is illustrated a colonic overtube 1 according to the invention for maintaining a section of a colon, in this case especially a sigmoid colon in a straightened configuration. The overtube 1 has a proximal end 2 for location, in use, externally of a colon, and a distal end 3 for insertion into a colon. A typical length for the overtube 1 is 0.5 m.

Figure 2:
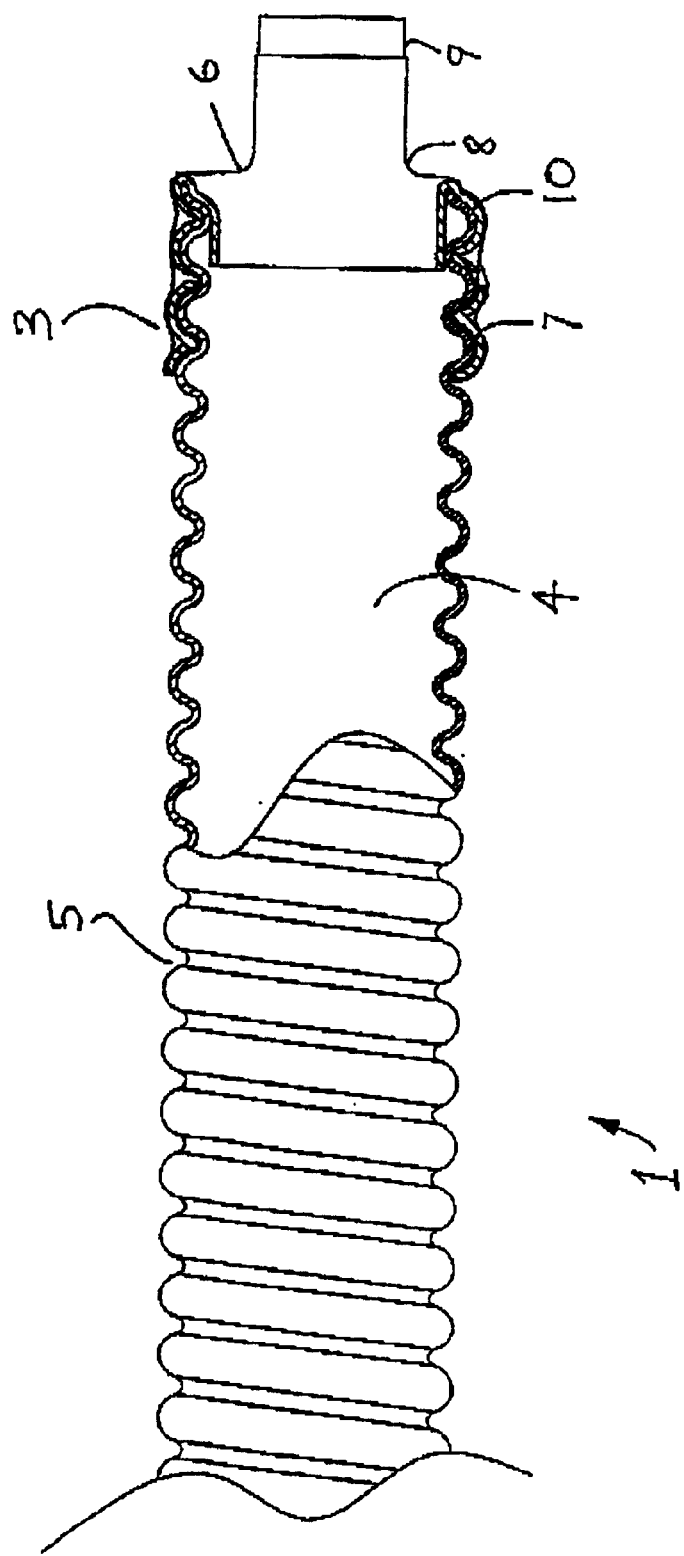
FIG. 2 is a partially cross-sectional, side view of a distal end of the overtube of FIG. 1.

A colonoscope lumen 4 extends through the overtube 1 to facilitate passing the overtube 1 over a colonoscope. At least portion of the overtube 1 is laterally flexible. In this manner the overtube 1 may flex substantially without kinking during advancement of the overtube 1 through a colon. In this case and as illustrated in FIGS. 1 and 2, the overtube 1 defines a corrugation 5 which is convoluted, the corrugation 5 extending along the entire length of the overtube 1 from the proximal end 2 to the distal end 3. The corrugated configuration of the overtube 1 minimises the possibility of the overtube 1 kinking as the overtube 1 is advanced over a colonoscope through a colon. As illustrated in particular in FIG. 2, in this case the corrugation 5 is provided on both the interior surface and the exterior surface of the overtube 1.

A flexible seal is provided at the distal end 3 of the overtube 1 for sealing between the overtube 1 and a colonoscope extending through the colonoscope lumen 4. The seal is in the form of a tubular sheath 6 of film, in this case silicone, material, which is fixed to an exterior surface of the overtube 1 at the distal end 3 of the overtube 1 by means of a section of heat-shrink tubing 7. As illustrated in FIG. 2, the sheath 6 extends inwardly at the distal end 3 of the overtube 1 for sealing between the overtube 1 and a colonoscope, and then distally of the distal end 3 of the overtube 1.

The sealing sheath 6 can evert from this distally extending configuration to a proximally extending configuration upon movement of the colonoscope relative to the overtube 1. This ensures a relatively large area of contact between the sheath 6 and the colonoscope which results in a secure seal between the colonoscope and the overtube 1.

The sheath 6 is folded over to define an inner sealing layer 9, and an outer sealing layer 8 around the inner sealing layer 9. The heat-shrink tubing 7 is provided between the inner and outer layers 9, 8 (FIG. 2).

The flexible nature of the seal 6 enables the seal 6 to adapt itself to the size of the colonoscope extending through the colonoscope lumen 4. In this manner, a secure, effective seal between the overtube 1 and a colonoscope is achieved regardless of the size diameter range of a colonoscope. In addition, the film seal 6 has a very low profile which facilitates easier passage of the overtube 1 over a colonoscope through a colon, while minimising the resultant discomfort to the patient.

The overtube 1 comprises another section of heat-shrink tubing 10 fixed to an exterior surface of the overtube 1 at the distal end 3 of the overtube 1. The tubing 10 extends around the distal end 3 of the overtube 1 partially into the colonoscope lumen 4 to define a rounded tip at the distal end 3 of the overtube 1. In this manner, the rounded tip tubing 10 ensures that there are no sharp edges at the distal end 3 of the overtube 1 for atraumatic advancement of the overtube 1 through a colon. The distal end 3 of the overtube 1 may be rounded off in a variety of different ways, such as by a separately mountable tip, or during the manufacturing process.

The overtube 1 is of a material which is thermally stable in use in a colon. In this case the thermally stable material used for the overtube 1 is polytetrafluoroethylene (PTFE)

In this manner, the overtube 1 is not overly stiff so that insertion of the overtube 1 into a colon, and navigation of the overtube 1 through a colon may be achieved without undue difficulty, and without causing undue discomfort to a patient. However once inserted into the colon, the stiffness of the overtube 1 remains above the minimum threshold of stiffness required to maintain a section of colon in a straightened configuration, and to prevent sigmoid loops from reforming as a colonoscope is passed through the colonoscope lumen 4.

A coating of a lubricious material such as a gel, for example a gel of silicone or polytetrafluoroethylene (PTFE) may be applied around the interior and/or exterior surfaces of the overtube 1 before use for ease of passage of the overtube 1 relative to a colonoscope and/or relative to a colon. Alternatively the coating of lubricious material may be provided as part of the overtube 1, such as by fixing the coating to the overtube 1, or by providing the coating integral with the overtube 1.

Figure 3:
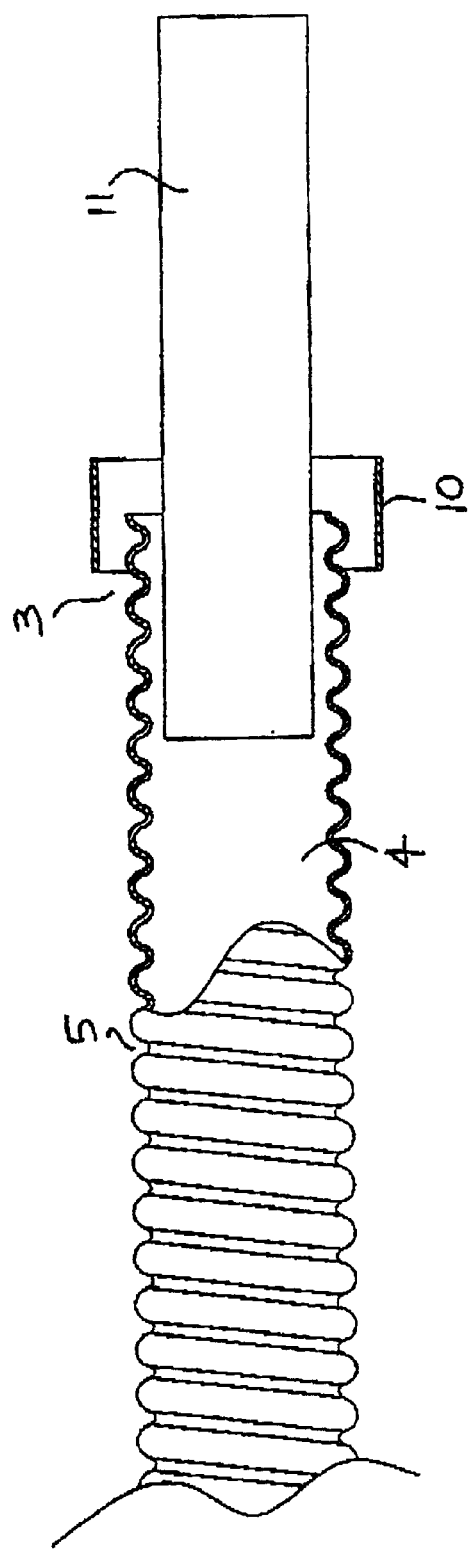
FIGS. 3 to 7 are partially cross-sectional, side views illustrating manufacture of the overtube of FIG. 2.
Figure 4:
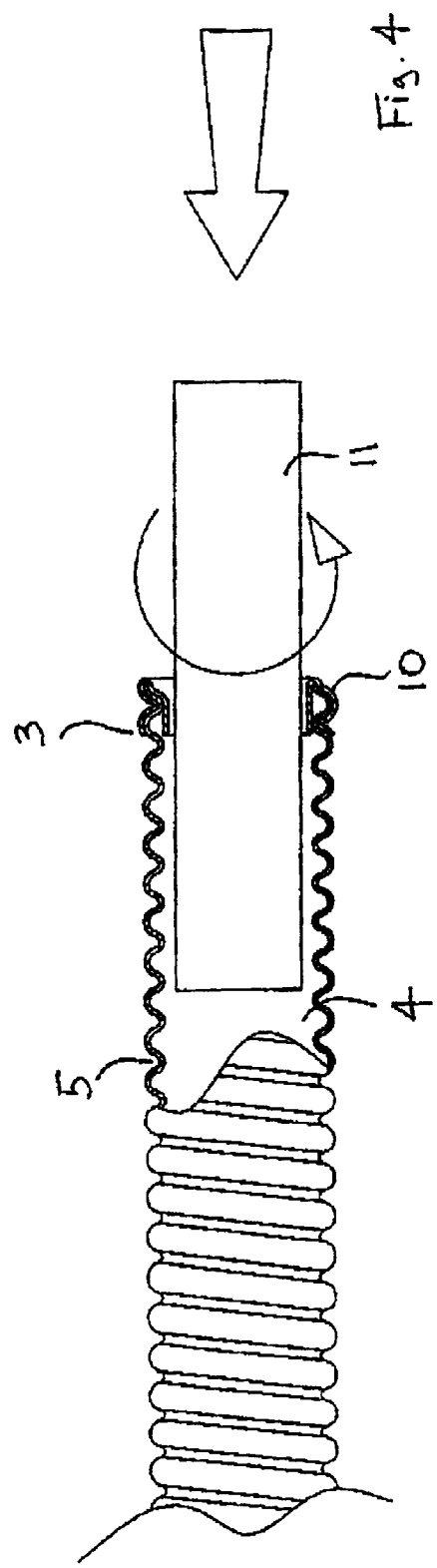
Figure 5:
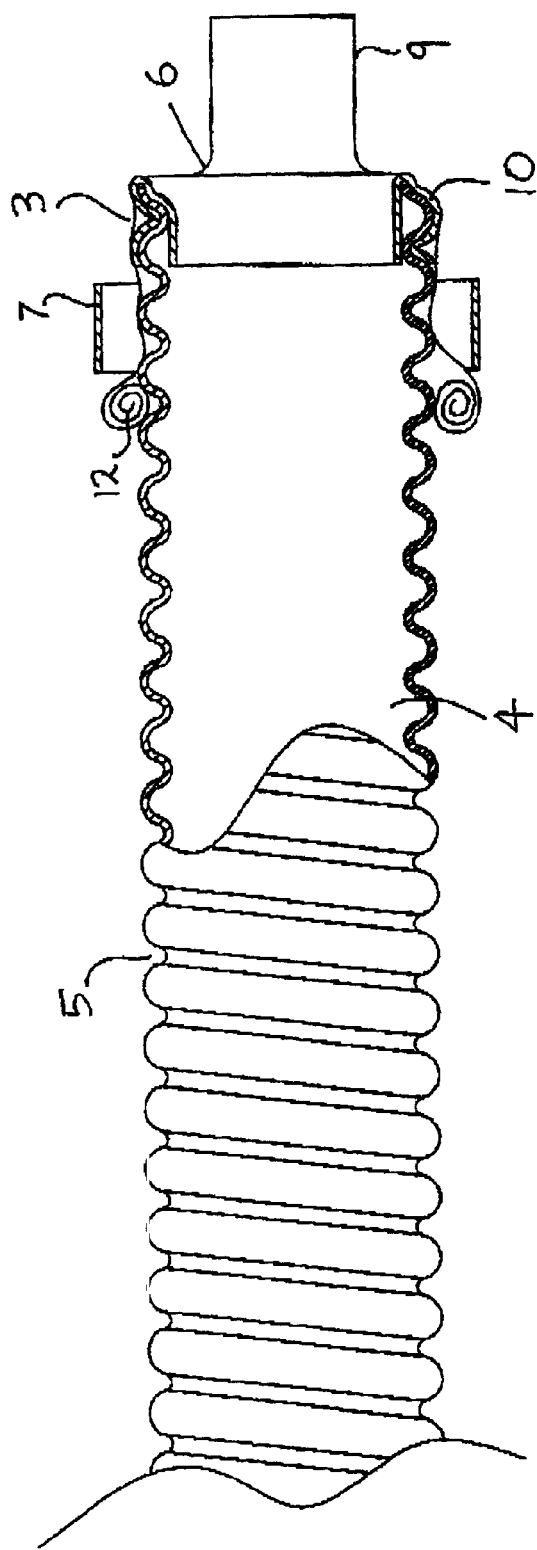

Manufacture of the overtube 1 will be described with reference to FIGS. 3 to 7. The overtube 1 is extruded to a typical length of 0.5 m with the convoluted corrugation 5 extending along the overtube 1 from the proximal end 2 to the distal end 3. The section of heat-shrink tubing 10 is positioned around the distal end 3 of the overtube 1, partially overlapping the distal end 3, and a mandrel 11 is partially inserted into the colonoscope lumen 4 from the distal end 3 (FIG. 3). Heat is applied to shrink the tubing 10 down partially onto the exterior surface of the overtube 1 and partially onto the mandrel 11. The mandrel 11 is moved further into the colonoscope lumen 4 while rotating the mandrel 11 (FIG. 4). By moving the mandrel 11 proximally, the tubing 10 is folded around the distal end 3 of the overtube 1 partially into the colonoscope lumen 4, and by rotating the mandrel 11, the tubing 10 is detached from the mandrel 11. The mandrel 11 is then removed from the colonoscope lumen 4.

Figure 6:
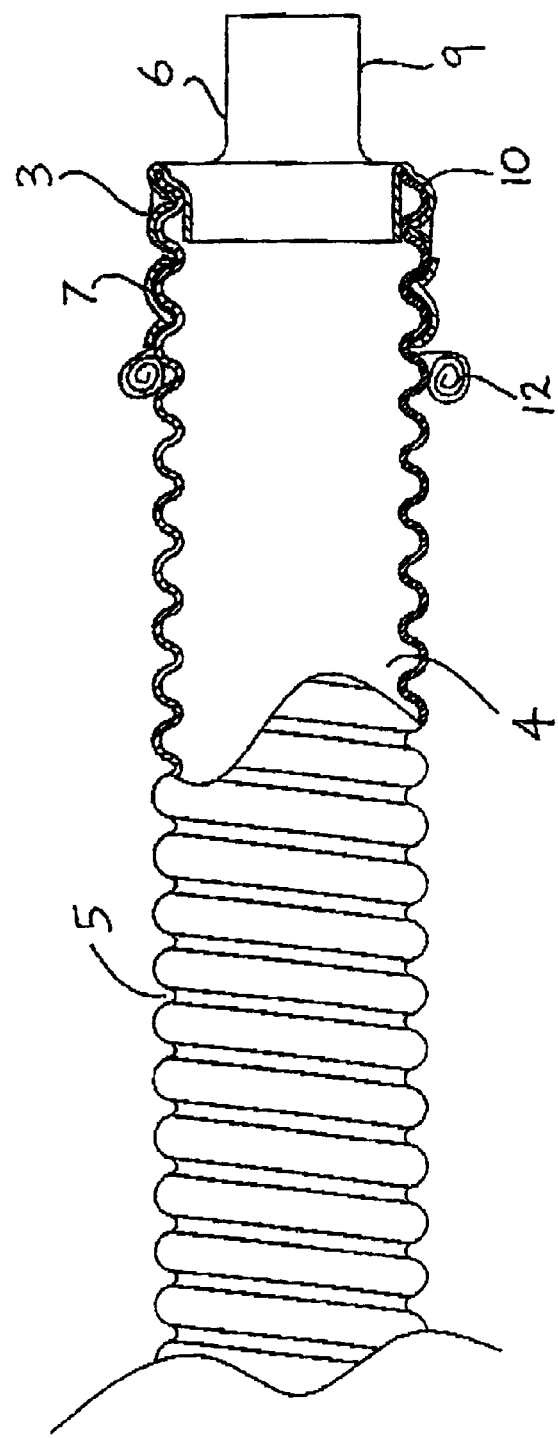
Figure 7:
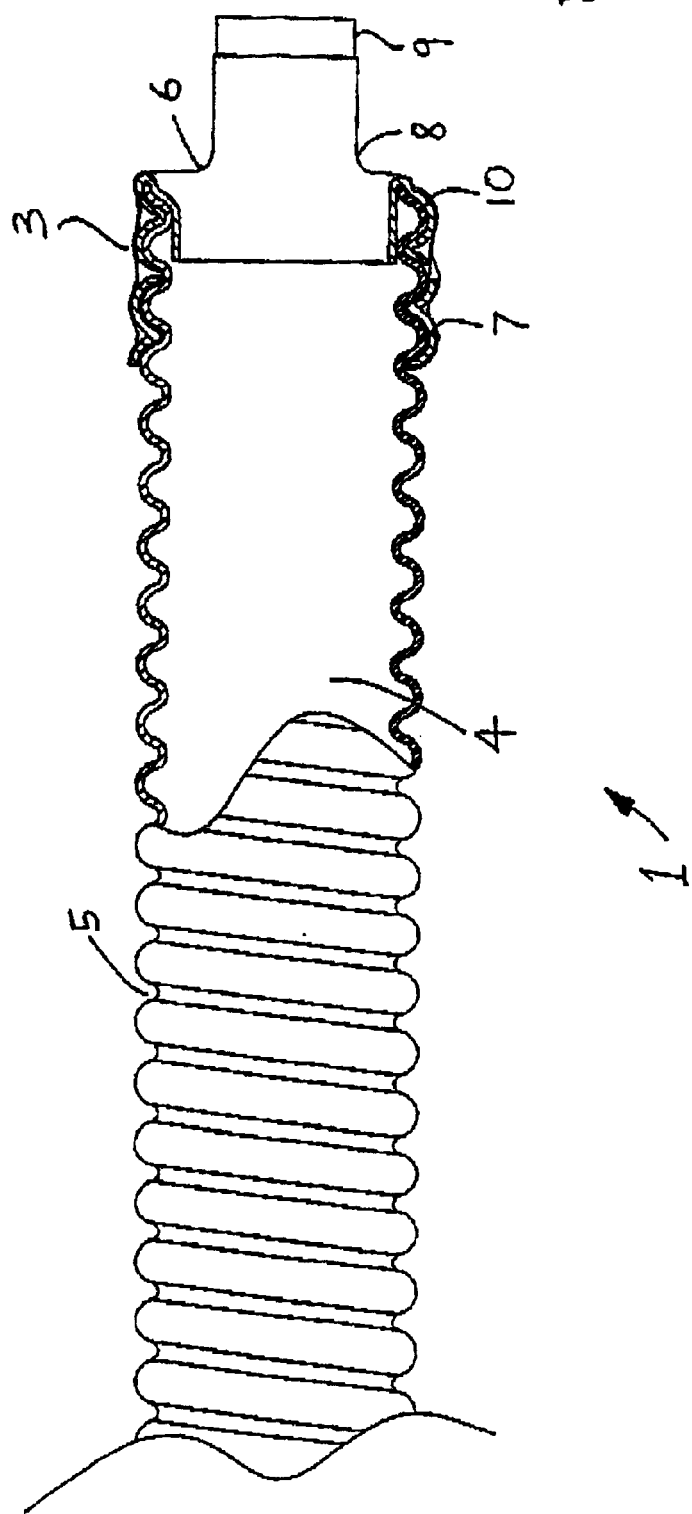
Figure 8:
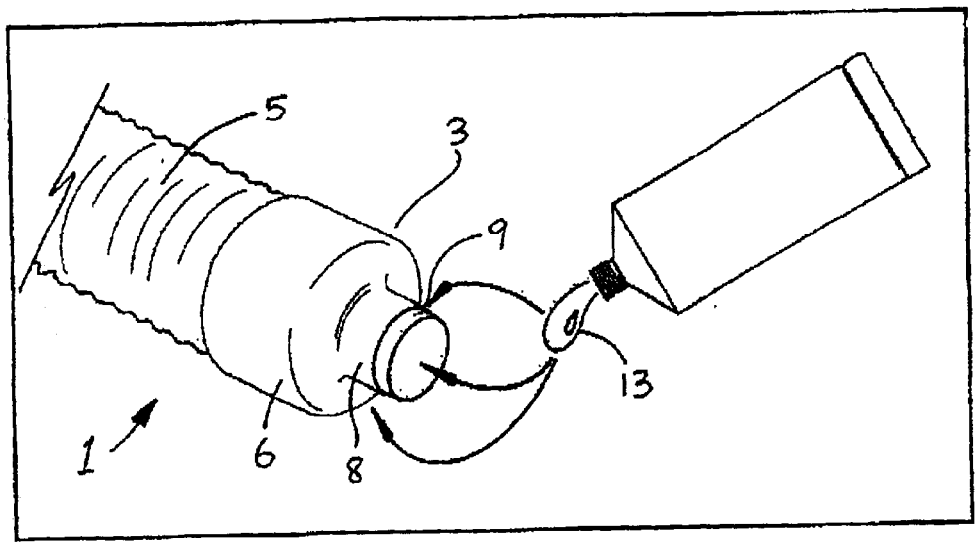
FIG. 8 is a schematic view illustrating lubrication of the overtube of FIGS. 1 and 2.

A proximal end 12 of the tubular sheath 6 is rolled inwardly, and the sheath 6 is positioned around the distal end 3 of the overtube 1, partially overlapping the distal end 3. The tubular sheath 6 has a smaller diameter than the overtube 1, so the sheath 6 is stretched to position it around the distal end 3 of the overtube 1. The section of the heat-shrink tubing 7 is positioned around the sheath 6 distally of the rolled proximal end 12 (FIG. 5), and heat is applied to shrink the tubing 7 down onto the sheath 6 to fix the sheath 6 to the exterior surface of the overtube 1 (FIG. 6). The rolled proximal end 12 is then rolled out distally over the tubing 7, off the distal end 3 of the overtube 1 to define the outer sealing layer 8 around the inner sealing layer 9 (FIG. 7).

Figure 9:
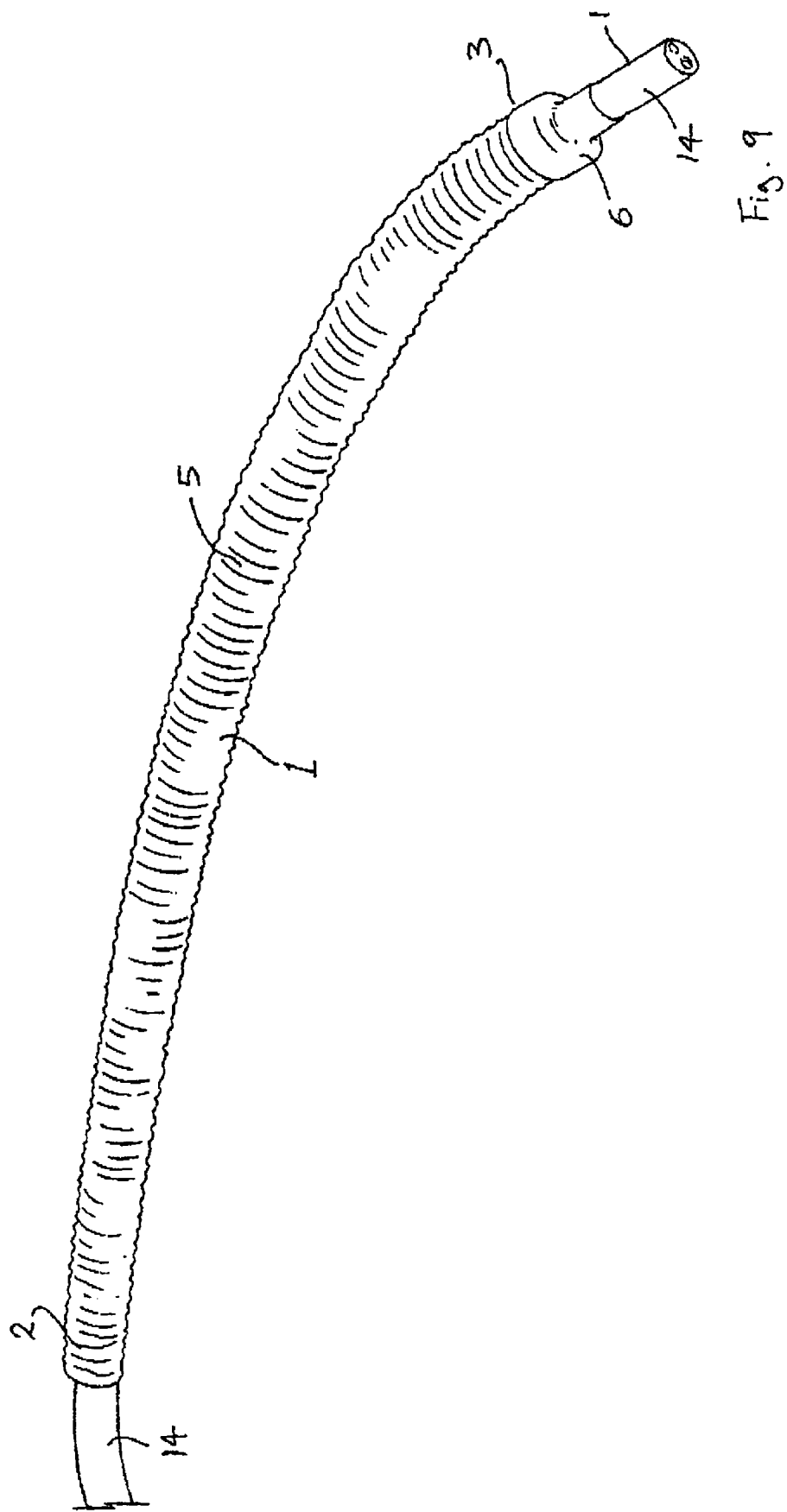
FIGS. 9 and 10 are perspective views of a colonoscope extending through the overtube of FIG. 1.

The assembled colonic overtube 1 is now ready for use. A biocompatible lubricant 13 is liberally applied both externally and internally to the overtube 1 (FIG. 8) to ease passage of the overtube 1 relative to a colonoscope and/or relative to a colon. A colonoscope 14 is inserted into the colonoscope lumen 4 at the proximal end 2 of the overtube 1 and advanced through the lumen 4 until a distal end 15 of the colonoscope 14 emerges from the distal end 3 of the overtube 1 through the sealing sheath 6 (FIG. 9).

Figure 10:
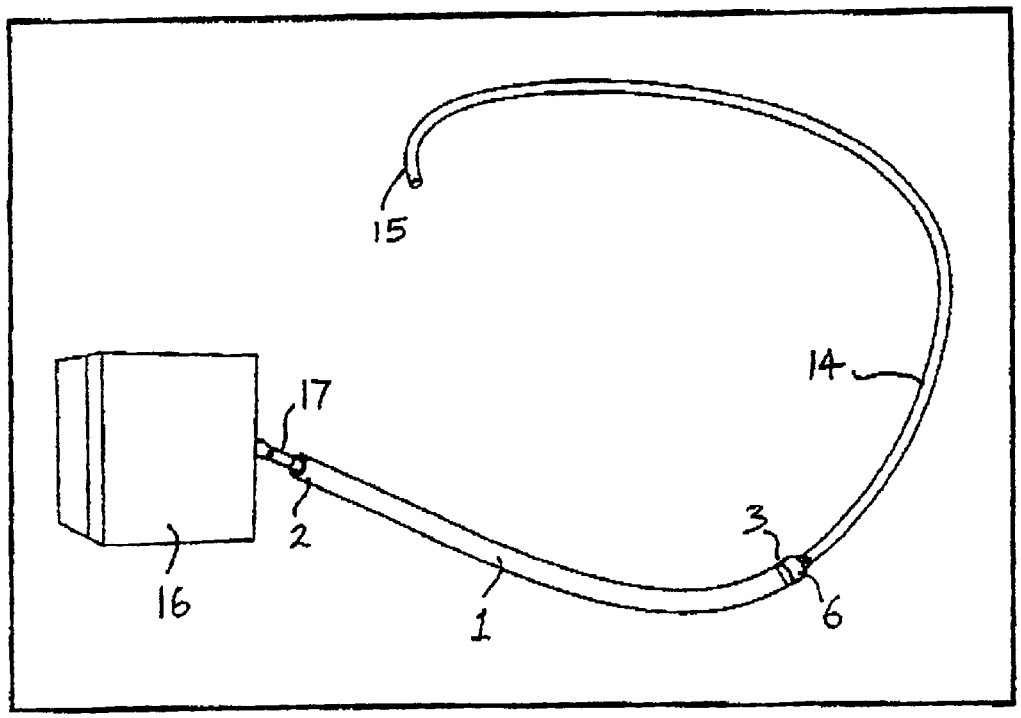

The colonoscope 14 has a power/light source 16 at a proximal end 17 of the colonoscope 14, and the overtube 1 is moved proximally over the colonoscope 14 until the proximal end 2 of the overtube 1 is adjacent the power/light source 16 (FIG. 10).

Figure 11:
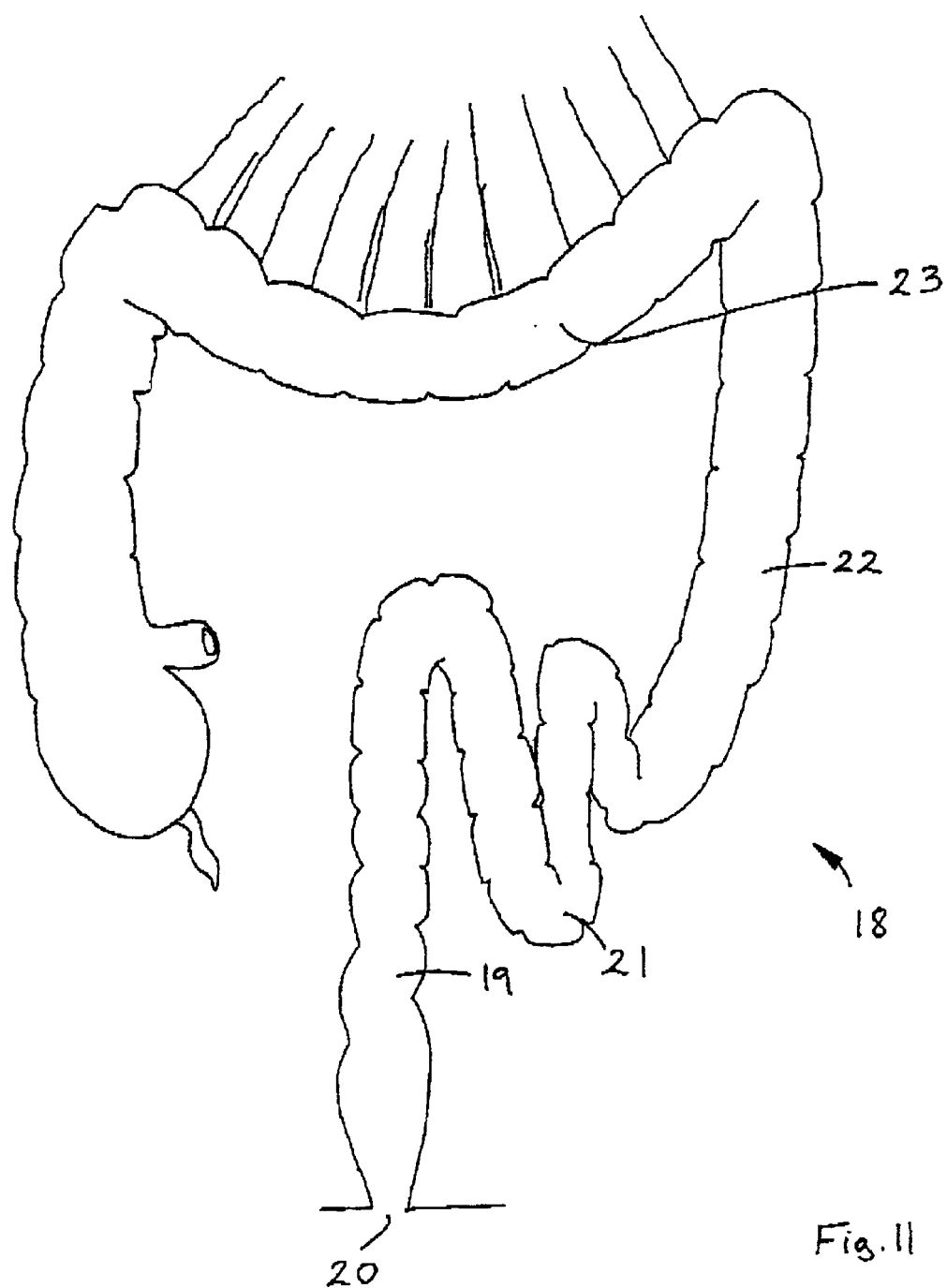
FIG. 11 is a schematic view of a colon.

The colonoscope 14 is now ready for insertion into the colon of a patient. A typical colon 18 is illustrated in FIG. 11, in which the rectum 19 leads from the anus 20 to the sigmoid colon 21. The redundancy in the sigmoid colon 21 may be seen in FIG. 11. The descending colon 22 leads from the sigmoid colon 21 to the transverse colon 23.

Figure 12:
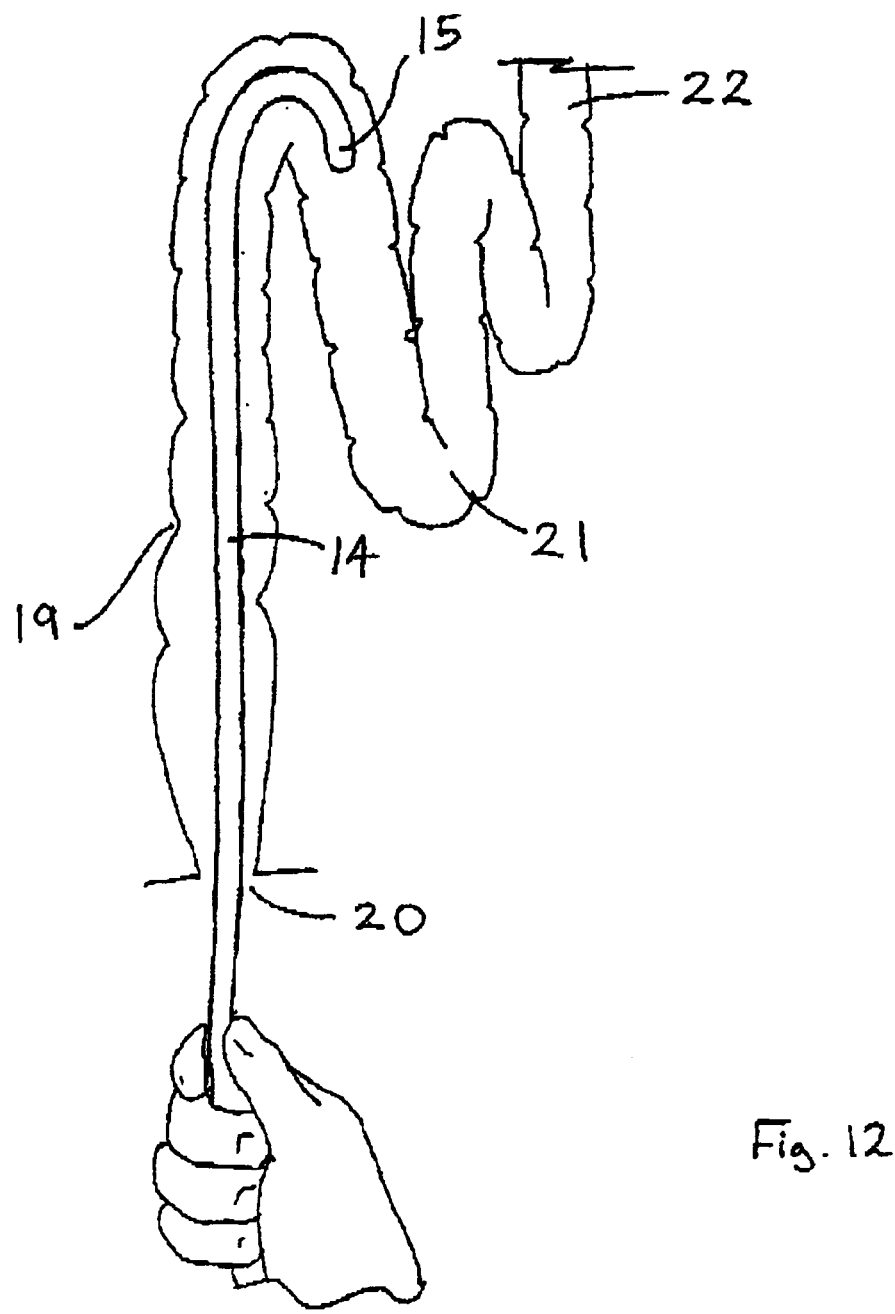
FIGS. 12 to 17 are schematic views of the colonoscope and overtube of FIGS. 9 and 10 in use in the colon of FIG. 11.
Figure 13:
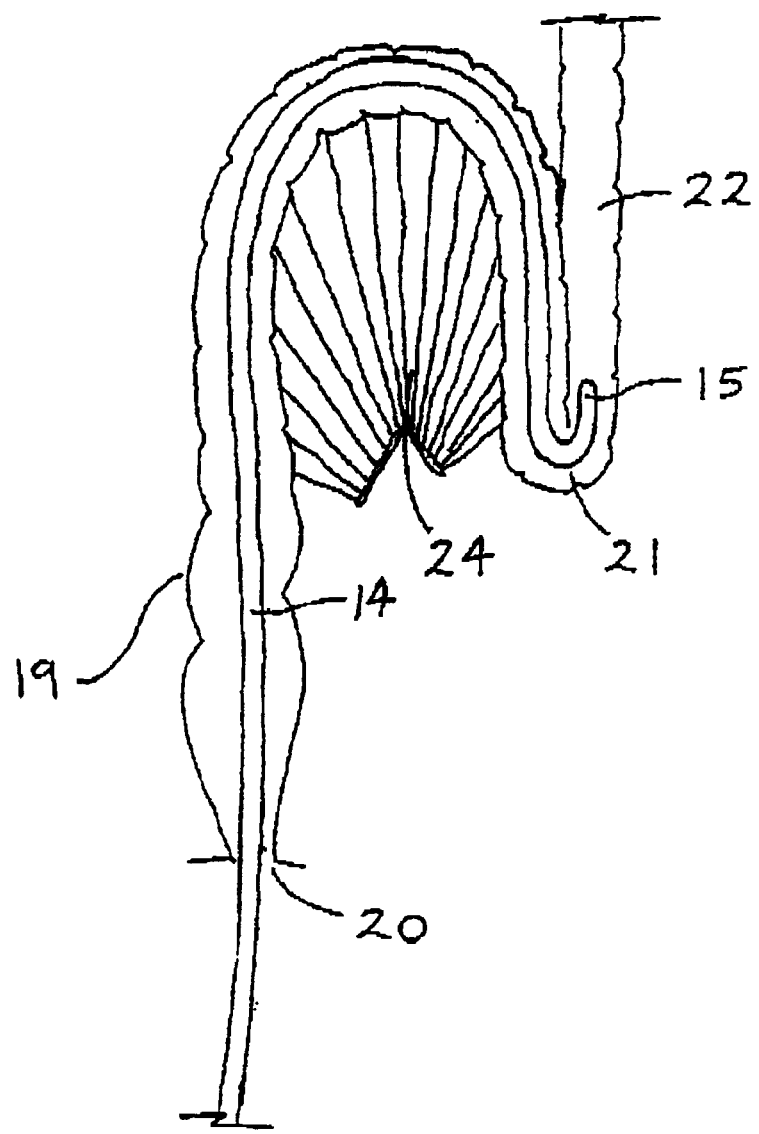
Figure 14:
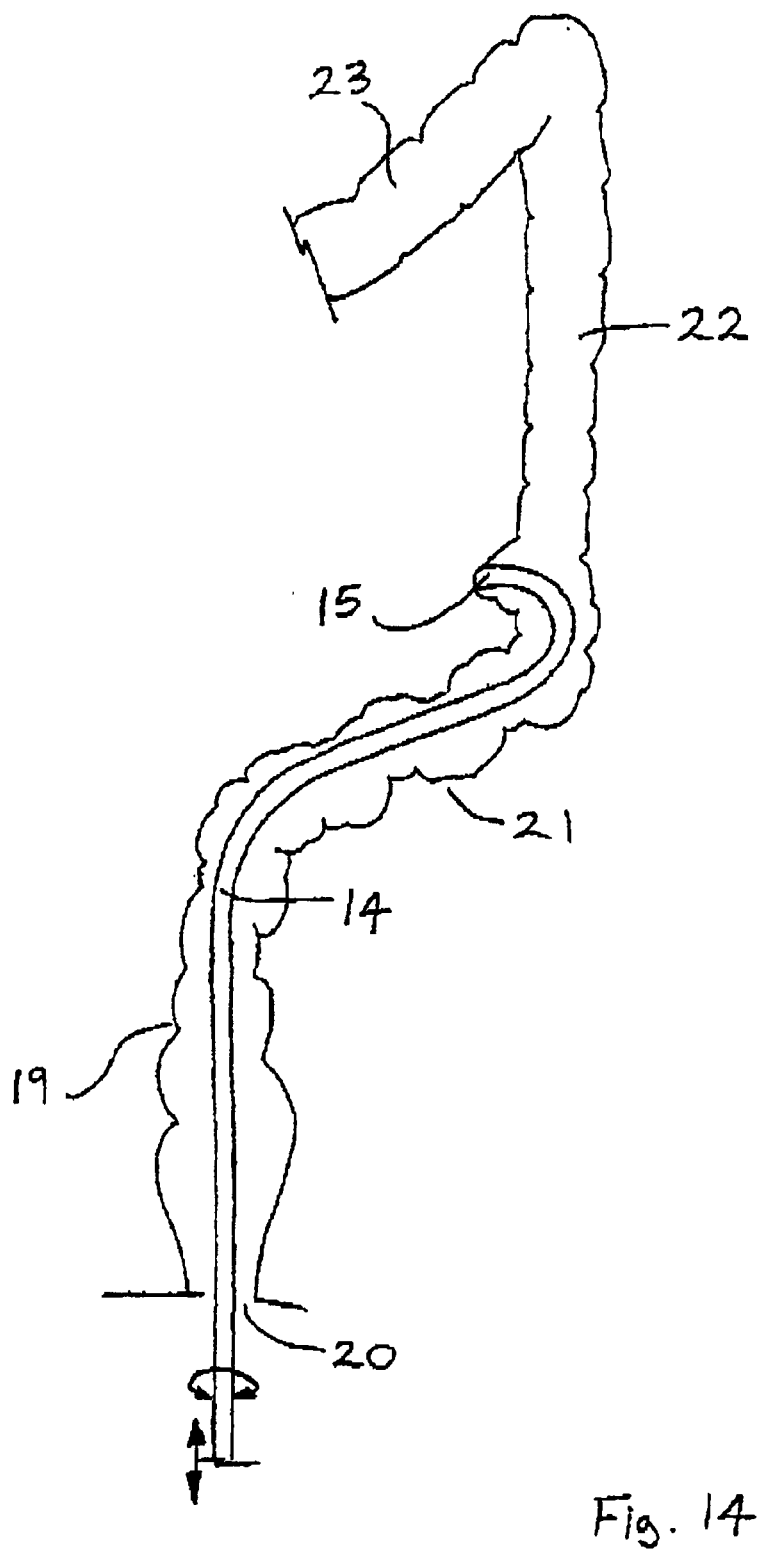
Figure 15:
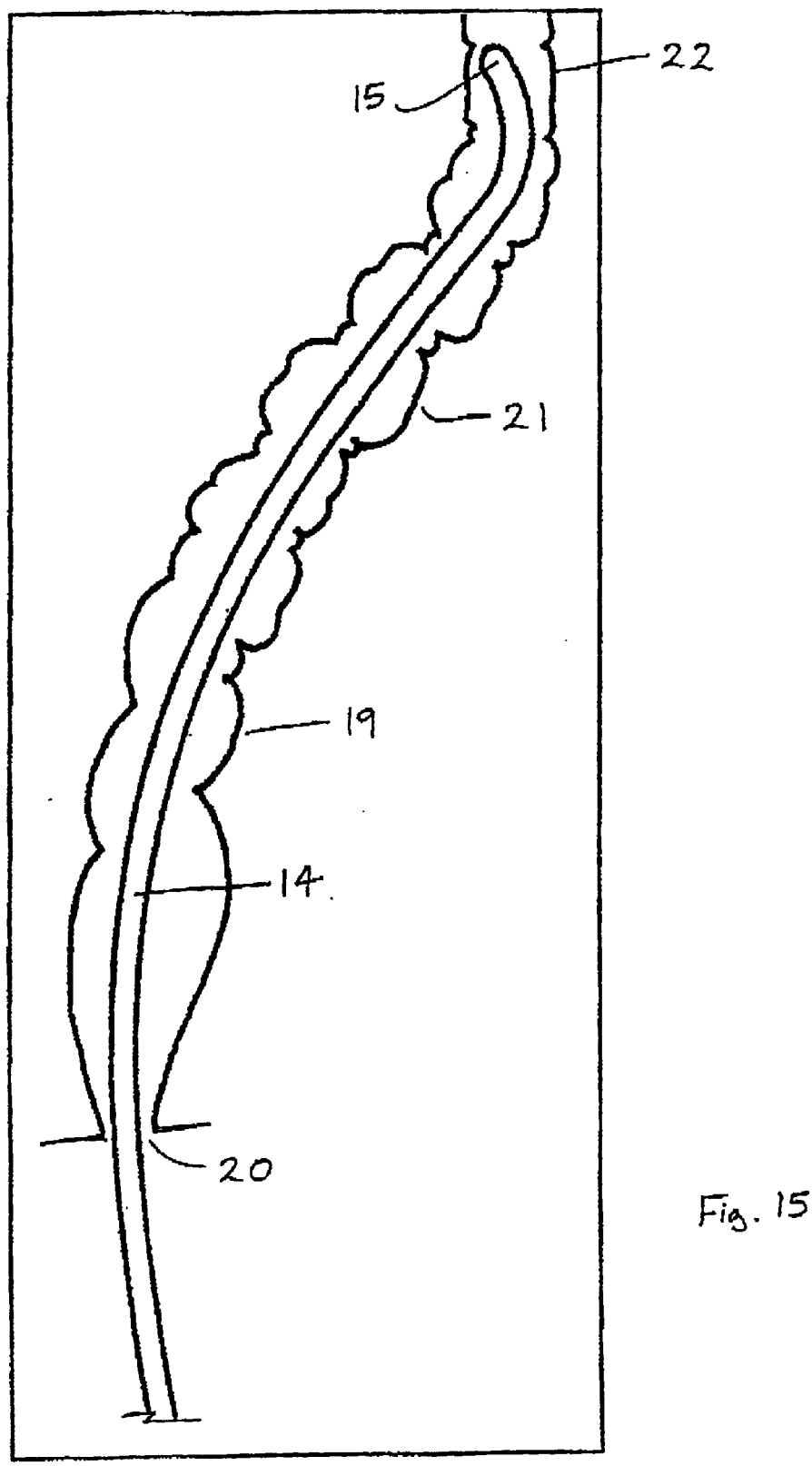

The distal end 15 of the colonoscope 14 is inserted through the anus 20 into the rectum 19, and the colonoscope 14 is advanced into the sigmoid colon 21 (FIG. 12). As the colonoscope 14 advances through the floppy sigmoid colon 21, a loop may form in the sigmoid colon 21, which results in stretching of the mesentery 24 to which the sigmoid colon 21 is attached (FIG. 13). When the distal end 15 of the colonoscope 14 reaches the proximal end of the descending colon 22, the distal end 15 is anchored in the fixed descending colon 22, and the sigmoid colon 21 is straightened by manipulating the colonoscope 14 (FIG. 14). When the sigmoid colon 21 has been straightened, the anchor is released (FIG. 15).

Figure 16:
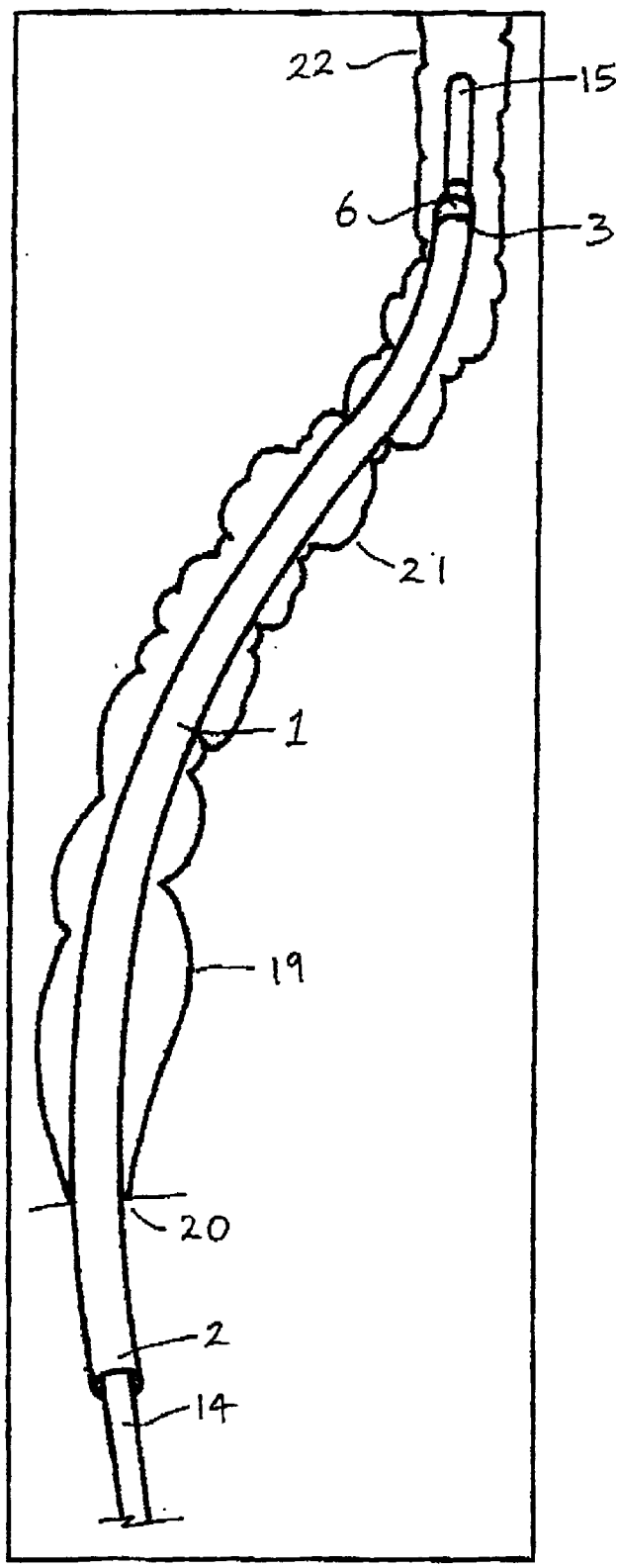

The distal end 3 of the overtube 1 is then inserted through the anus 20 into the rectum 19, and the overtube 1 is advanced through the straightened sigmoid colon 21 until the distal end 3 of the overtube 1 is at the proximal end of the descending colon 22 (FIG. 16). The overtube 1 is then advanced through the colon 18 over the colonoscope 14, as illustrated in FIG. 16. In this manner, the colonoscope 14 acts as a guiding track for the overtube 1 as it advances through the colon 18.

The sheath 6 effects a double-layered seal between the overtube 1 and the colonoscope 14 at the distal end 3 of the overtube 1. This seal ensures that no parts of the interior wall of the colon 18 become trapped between the colonoscope 14 and the overtube 1 as the overtube 1 is advanced over the colonoscope 14, and thus prevents shearing off of any parts of the colon wall, or puncturing the colon wall, or any other damage to the interior wall of the colon 18. The sealing sheath 6 also presents faeces or other bodily materials leaking between the colonoscope 14 and the overtube 1 proximally out through the anus 20.

Figure 17:
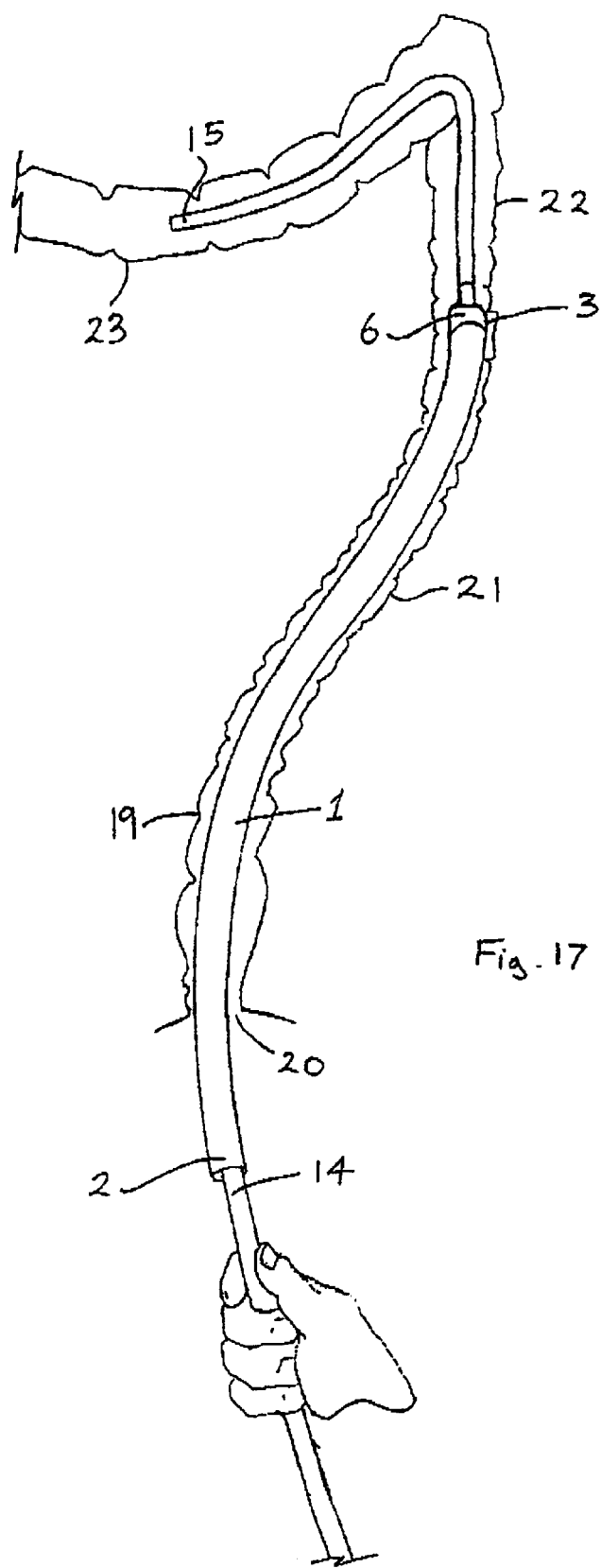

With the overtube 1 extended through the straightened sigmoid colon 21, as illustrated in FIG. 16, the colonoscope 14 may then be advanced further distally through the descending colon 22 and into the transverse colon 23 (FIG. 17). The overtube 1 acts as a splint to maintain the sigmoid colon 21 in the straightened configuration.

The splinting overtube 1 ensures that further advancement of the colonoscope 14 through the descending colon 22 and into the transverse colon 23 is possible by preventing loops from reforming in the sigmoid colon 21. In this manner, the overtube 1 minimises the pain or discomfort experienced by the patient during this procedure.

Figure 29:
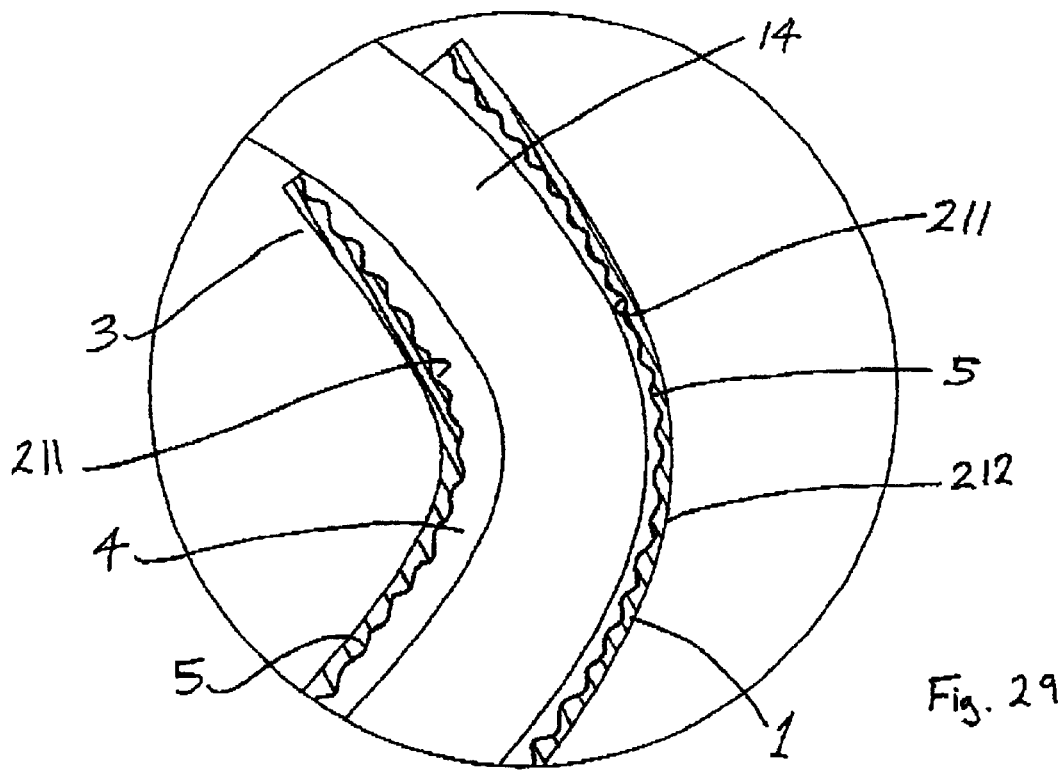
FIG. 29 is an enlarged, partially cross-sectional, side view of part of the colonoscope and overtube of FIG. 28.
Figure 30:
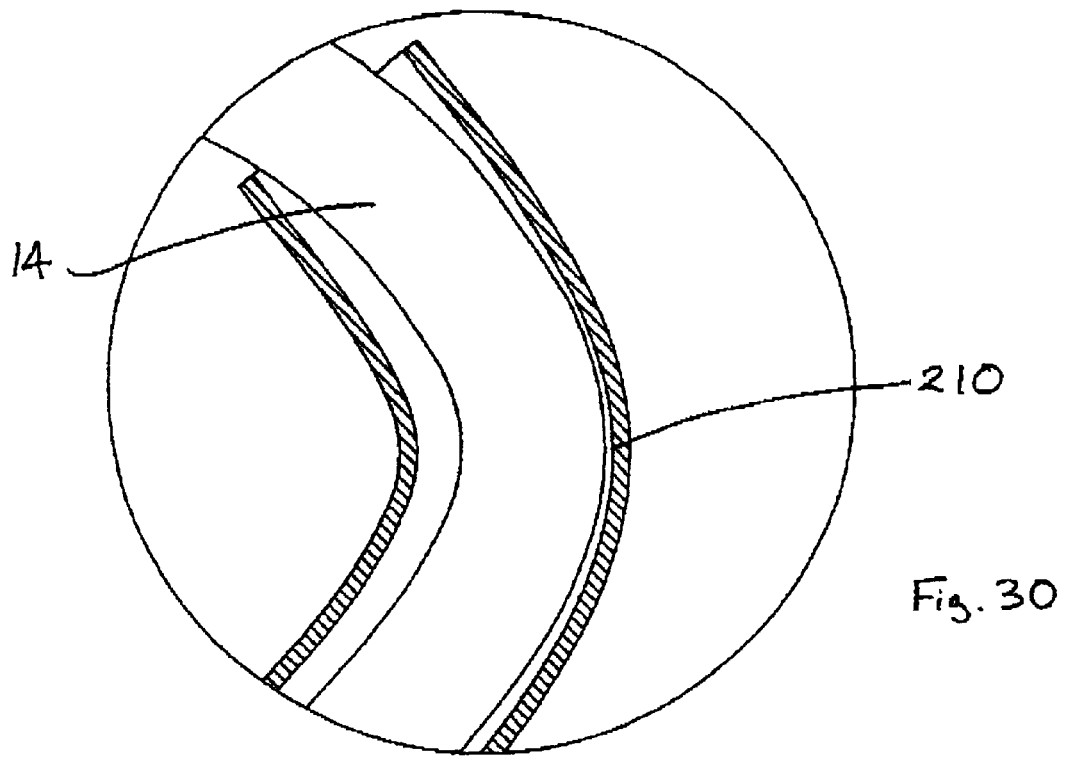
FIG. 30 is a partially cross-sectional, side view of the colonoscope of FIG. 29 advancing through another overtube.

In addition, the corrugation 5 which extends along the overtube 1 in a convoluted manner results in a discontinuous interior surface 211 of the overtube 1, as illustrated in FIG. 29. The corrugation 5 projects inwardly for contacting the colonoscope 14 in the colonoscope lumen 4. Thus, as the colonoscope 14 is advanced through the overtube 1, the area of contact between the colonoscope 14 and the corrugated overtube 1 is less than the area of contact that would otherwise result with a continuous interior surface 210, as illustrated in FIG. 30. Because the area of contact between the colonoscope 14 and the corrugated overtube 1 is reduced, the frictional force acting between the colonoscope 14 and the corrugated overtube 1 is also reduced. In this manner, the corrugated overtube 1 enables an easier passage of the colonoscope 14 through the colonoscope lumen 4 of the overtube 1.

The exterior surface 212 of the overtube 1 may be smooth, as illustrated in FIG. 29. This smooth surface 212 reduces the discomfort and/or pain experienced by the patient during the colonoscopy procedure while maintaining the kink-resistant and low-friction properties of the corrugation 5 on the interior surface 211.

Figure 31:
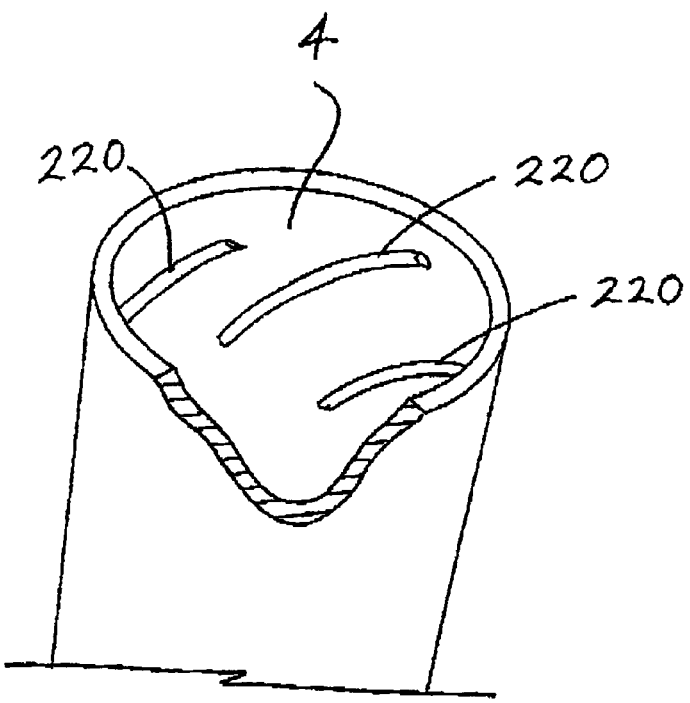
FIGS. 31 and 32 are partially cut-away, perspective views of other overtubes according to the invention.
Figure 32:
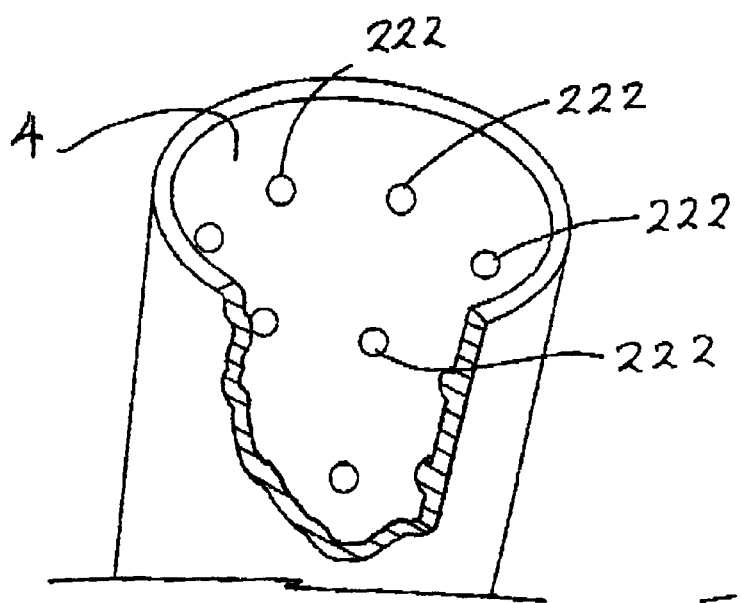

It will be understood that the discontinuous nature of the interior surface of the overtube of the invention may be achieved in any suitable manner. For example, the overtube may comprise one or more inwardly projecting elements in the form of protruding strips 220, as illustrated in FIG. 31. The strips 220 may extend longitudinally along the overtube, or along the overtube in a convoluted manner, or may extend at least partially circumferentially around the overtube. Alternatively the inwardly projecting elements may be provided in the form of a plurality of discrete protrusions 222, as illustrated in FIG. 32. By contacting a colonoscope in the colonoscope lumen 4, the inwardly projecting elements 220, 222 reduce the fictional force acting between the overtube and the colonoscope, and thus ease passage of the overtube over the colonoscope.

It will be appreciated that the corrugated overtube may be provided in alternative forms to that described above. For example, the corrugation on the overtube may extend at least partially circumferentially around the overtube, and/or more than one corrugation may be provided on the overtube.

FIG. 33 illustrates another colonic overtube 230 according to the invention, which is similar to the overtube 1, and similar elements in FIG. 33 are assigned the same reference numerals. In this case, the overtube 230 comprises a reinforcement means, in the form of a coil 231 of metallic material embedded within the wall 232 of the overtube 230. This composite construction enables the overtube 230 to flex laterally during advancement over a colonoscope through a potentially tortuous path in a colon substantially without kinking.

It will be understood that the reinforcement means may be provided in any suitable form, such as a mesh, or a braided construction. In another alternative the composite overtube may have a layered construction.

It is to be understood that other configurations and constructions of overtube are also possible which are laterally flexible to facilitate flexing of the overtube substantially without kinking during advancement of the overtube through a colon.

More than one laterally flexible portion may be provided spaced along the overtube. The positioning and/or number of the laterally flexible portions may be selected to achieve the desired kink resistance.

Figure 25:
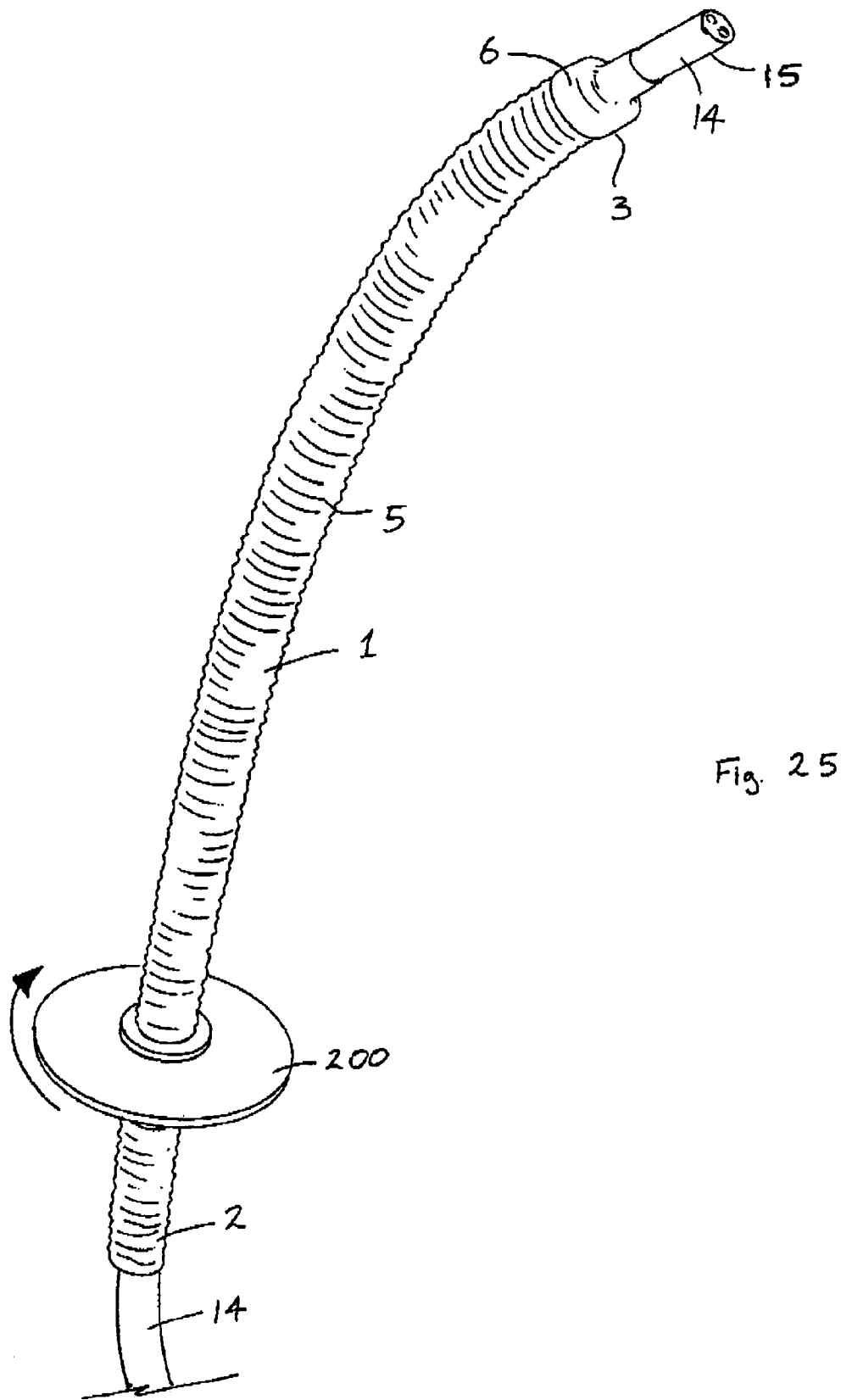
FIG. 25 is a perspective view of the colonoscope and overtube of FIG. 9 with a limiting means mounted to the overtube.
Figure 27:
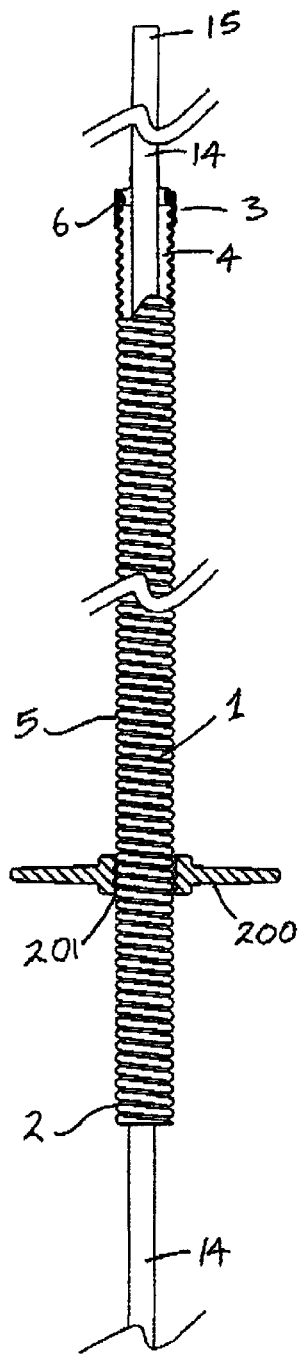
FIGS. 26 and 27 are partially cross-sectional, side views of the colonoscope, overtube and limiting means of FIG. 25.
Figure 26:
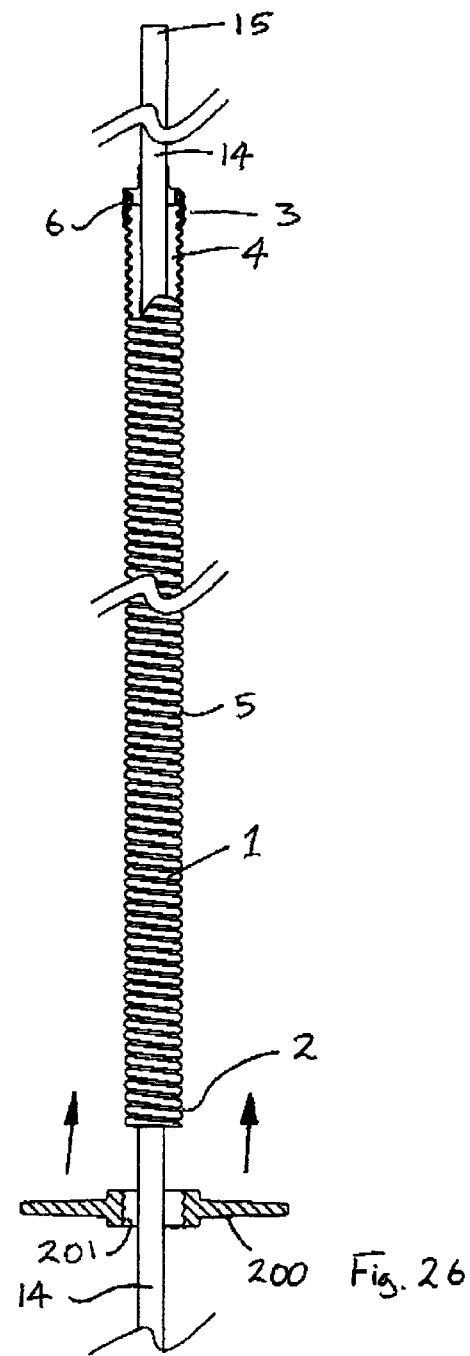
Figure 28:
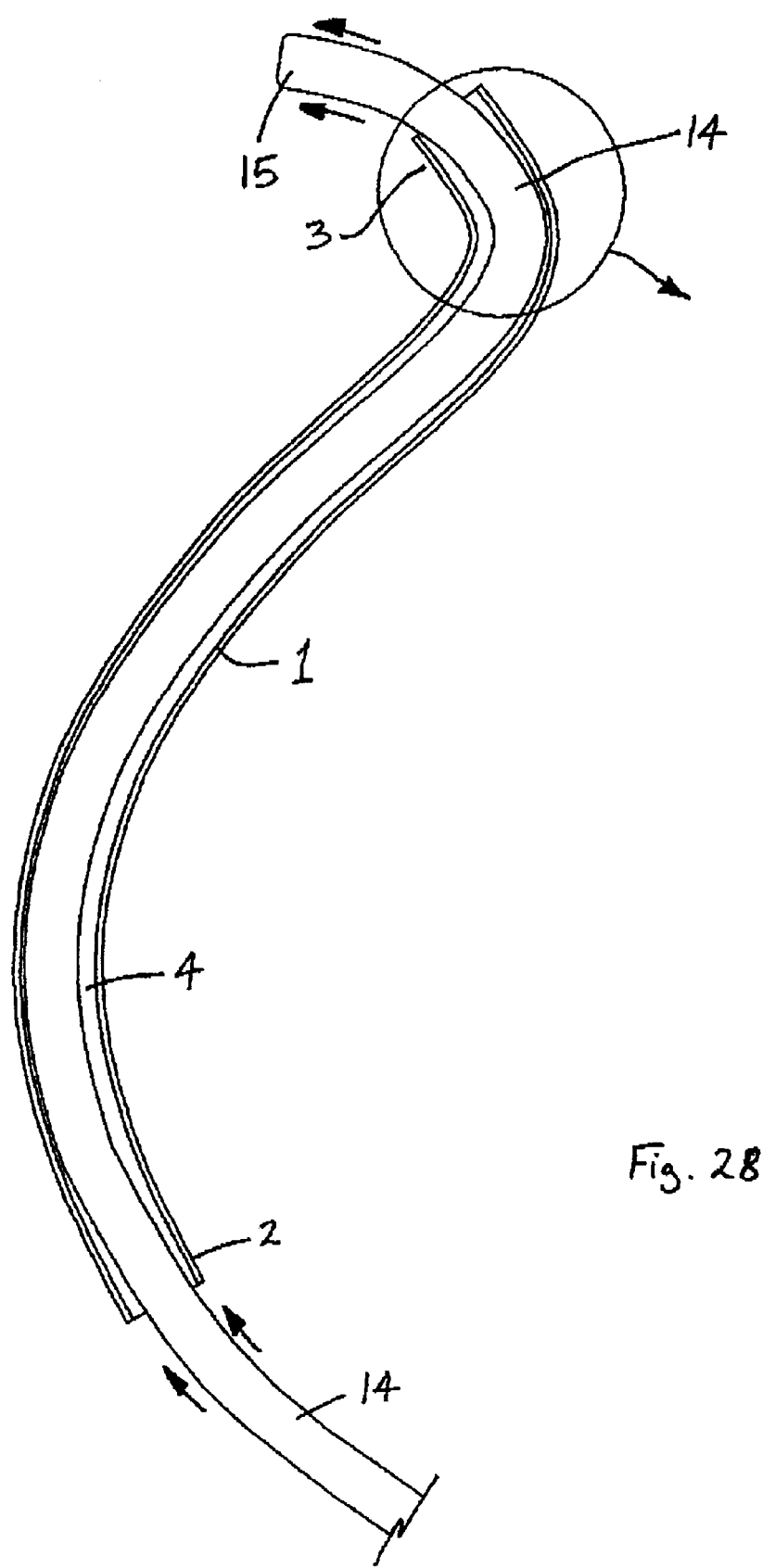
FIG. 28 is a partially cross-sectional, side view of the colonoscope of FIG. 9 advancing through the overtube of FIG. 9.

Referring to FIGS. 25 to 27, there is illustrated a flange 200 which may be used with the overtube 1 to prevent complete insertion of the overtube 1 into the colon 18. The flange 200 is releasably mounted to the overtube 1, in this case by means of a threaded arrangement 201.

The threaded mounting arrangement enables the position of the flange 200 on the overtube 1 to be adjusted by a simple rotation of the flange 200 relative to the overtube 1, as illustrated in FIGS. 26 and 27. Because the flange position is adjustable the colonoscopist can quickly and effectively adjust the flange 200 to suit the particular characteristics of the colon 18 undergoing treatment.

It will be appreciated that the flange 200 may be provided with alternative means of adjusting the position on the overtube 1, and/or with alternative means of releasable mounting to the overtube 1. Also the flange 200 could alternatively be provided fixed to or integral with the overtube 1 towards the proximal end 2 of the overtube 1. Furthermore, the limiting means may be provided in an alternative form to a flange.

Figure 18:
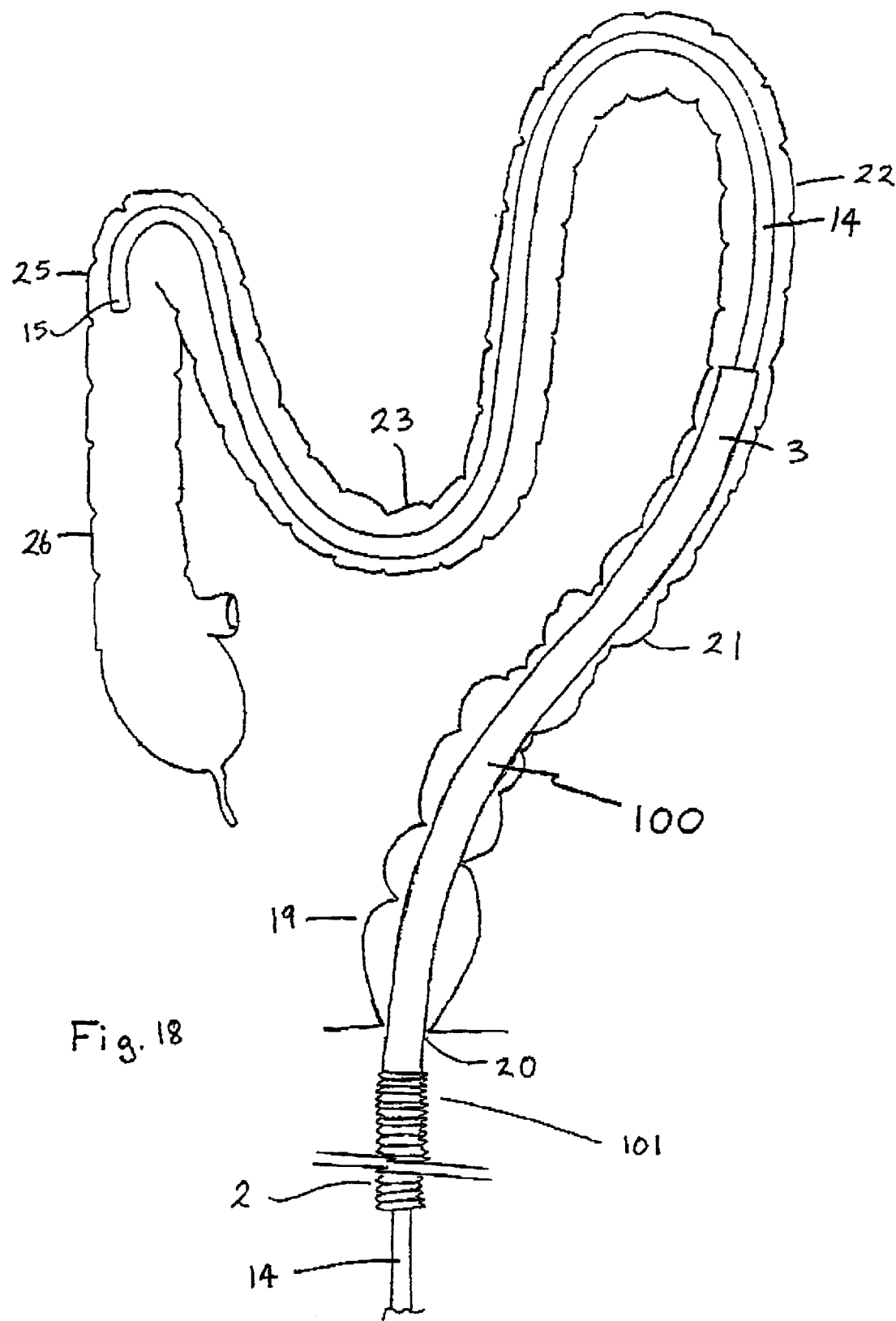
FIGS. 18 to 23 are schematic views of another colonic overtube according to the invention in use in the colon of FIG. 11.
Figure 19:
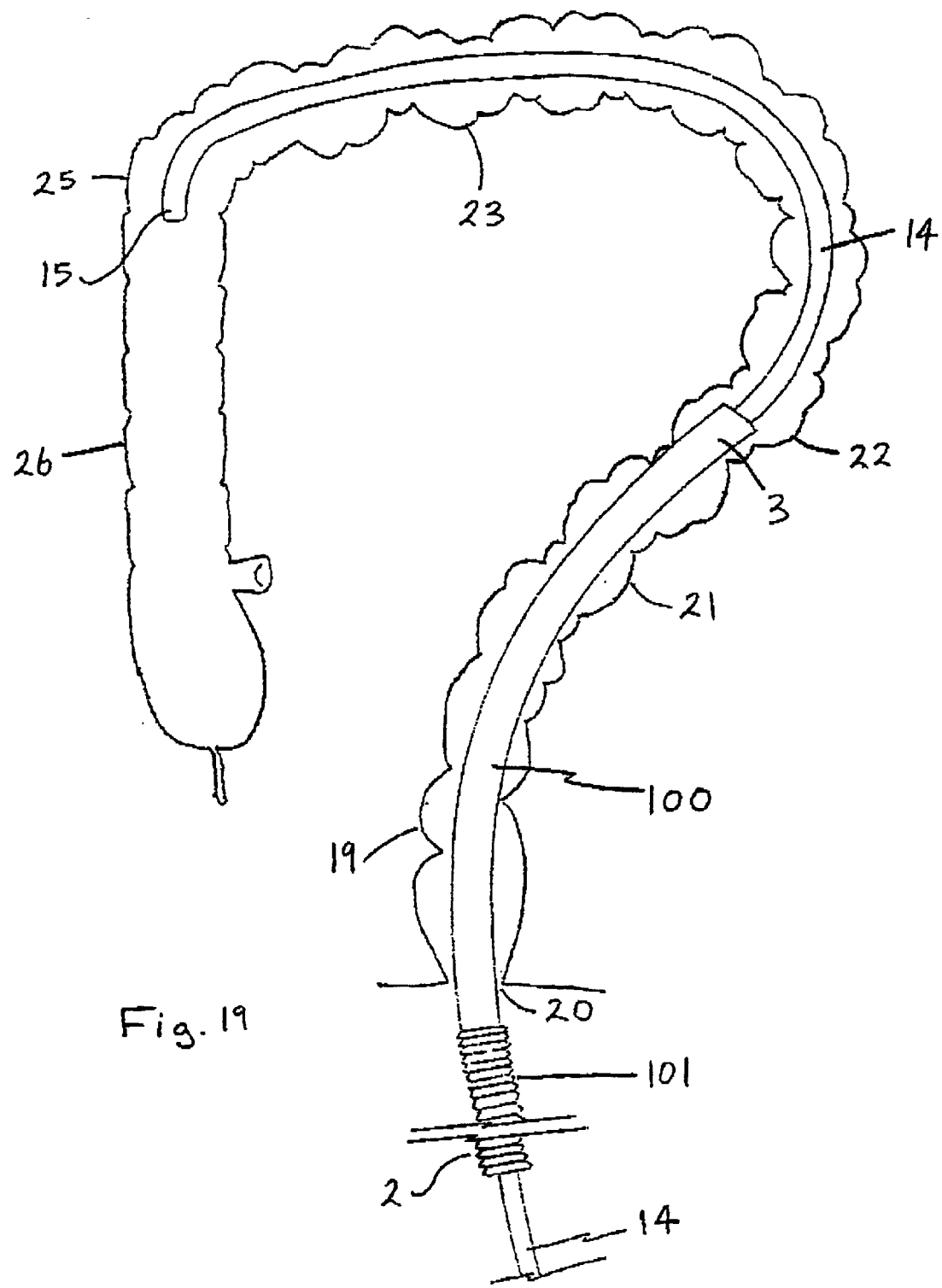
Figure 20:
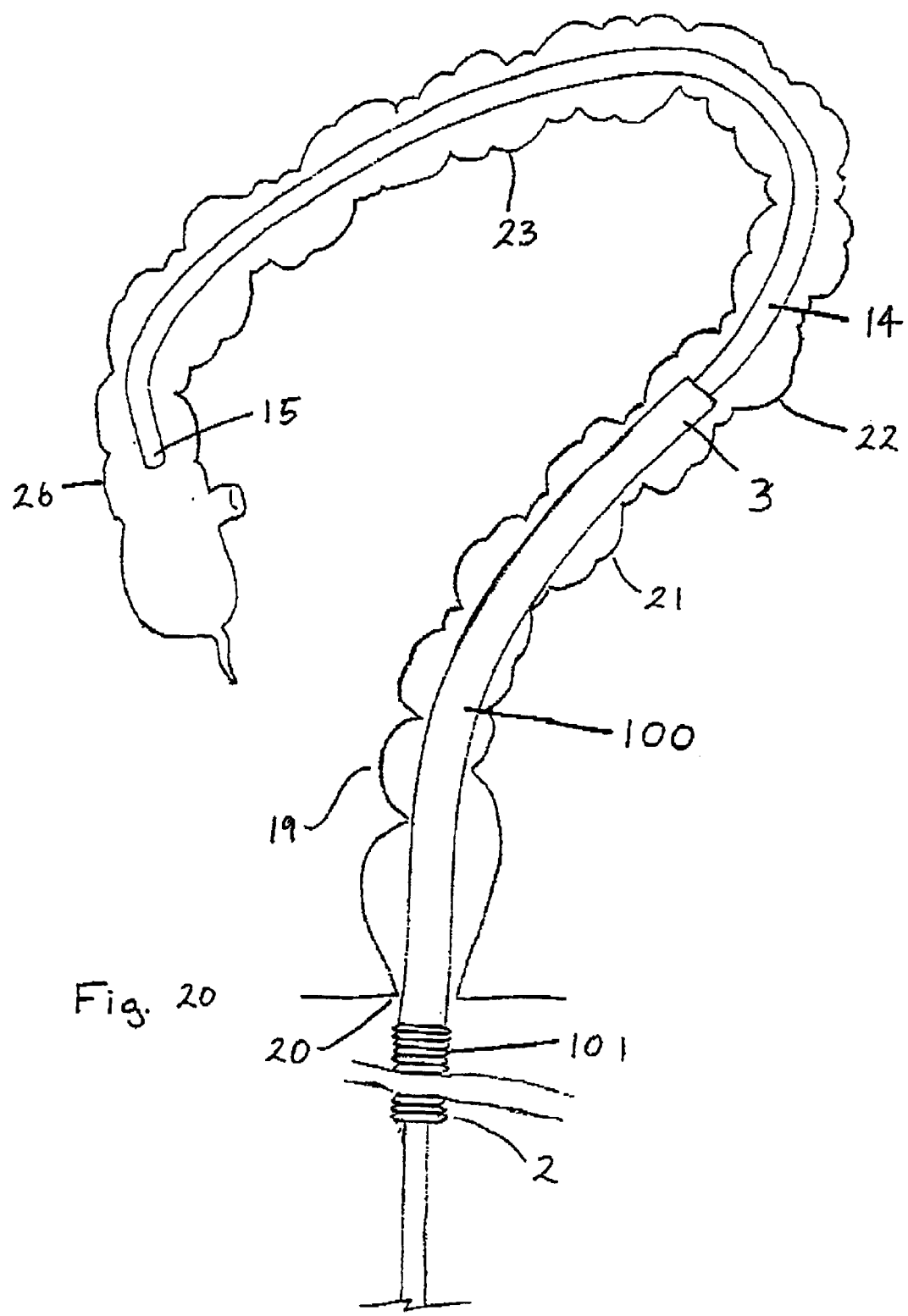
Figure 21:
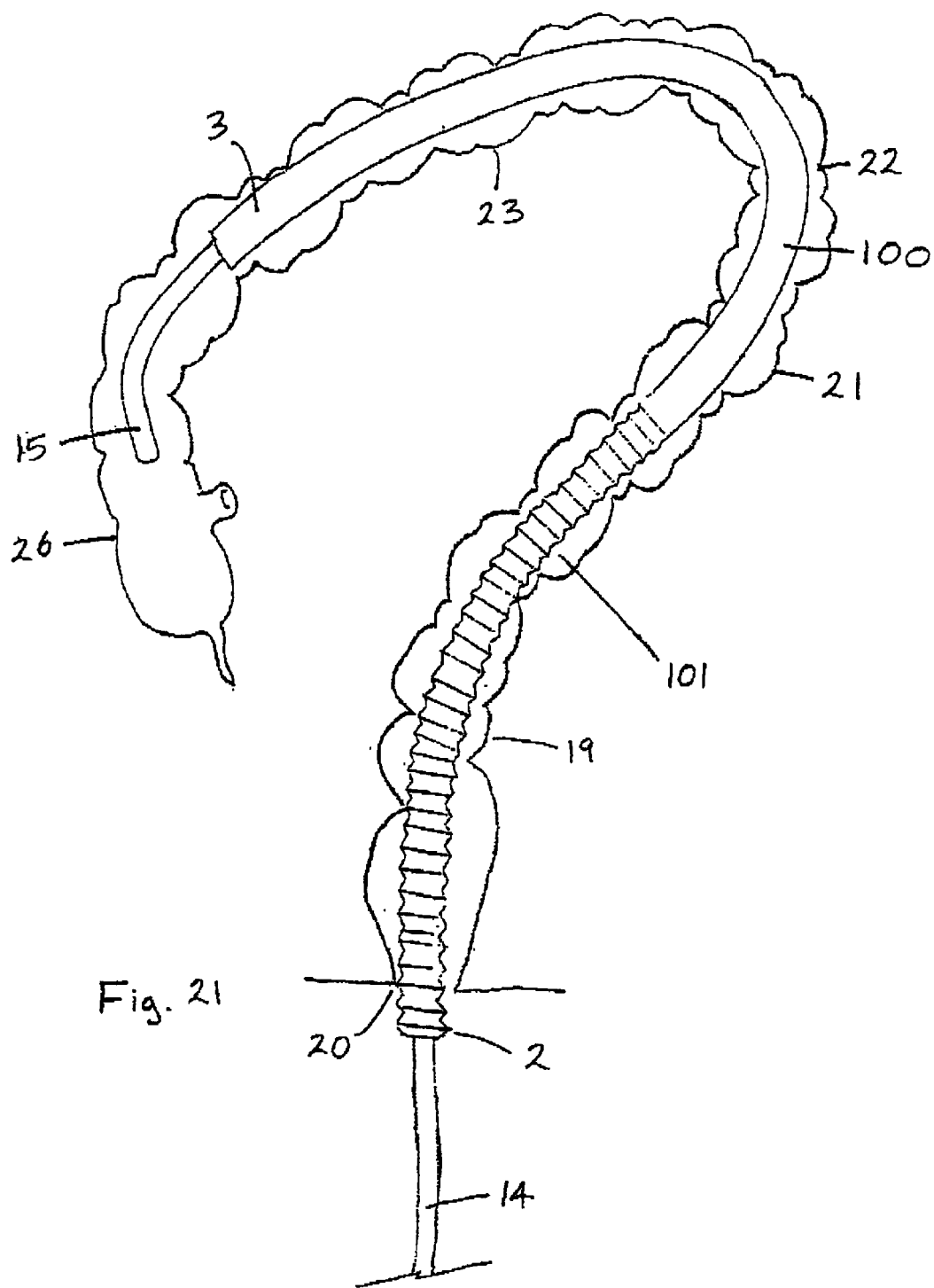
Figure 22:
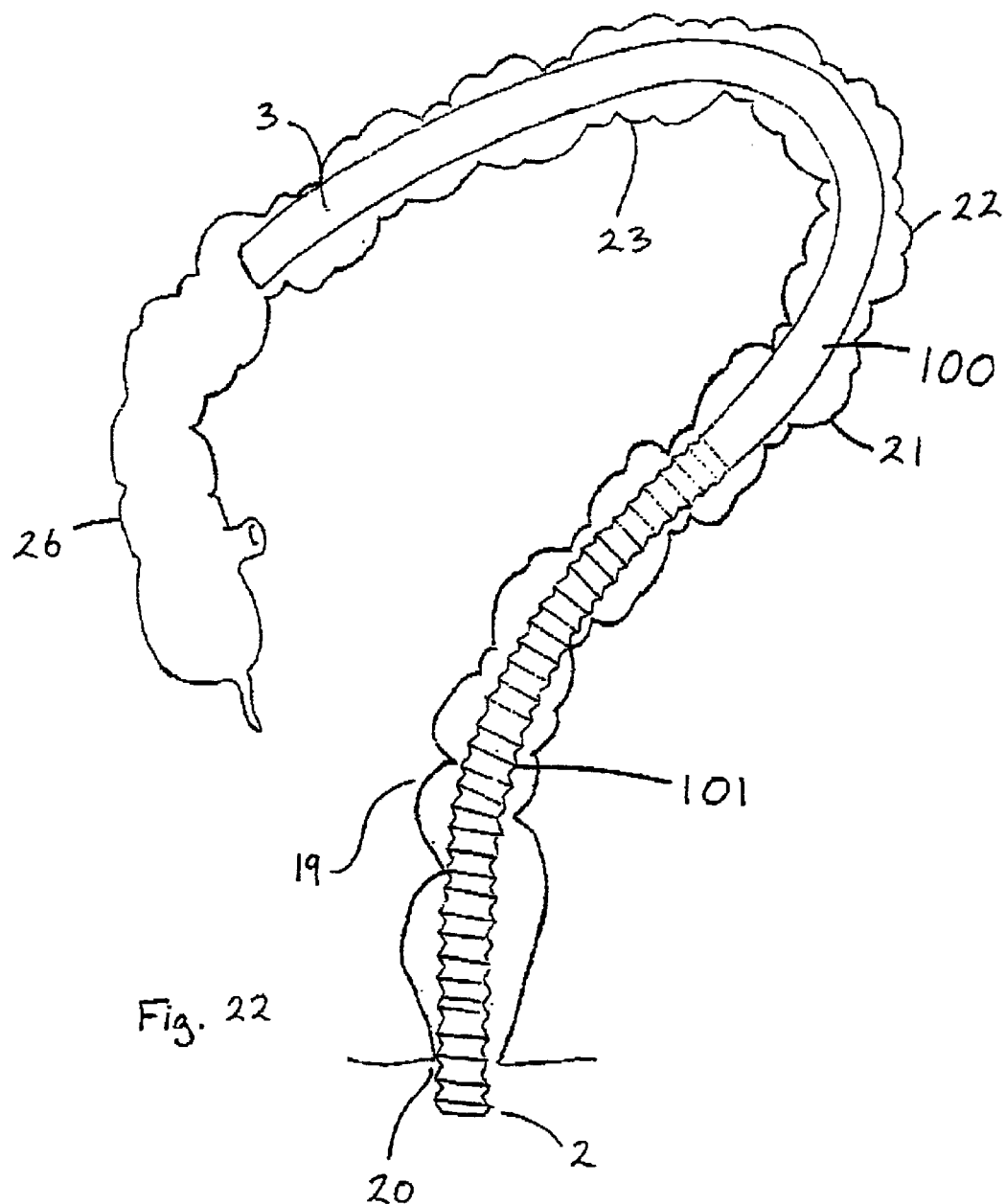
Figure 23:
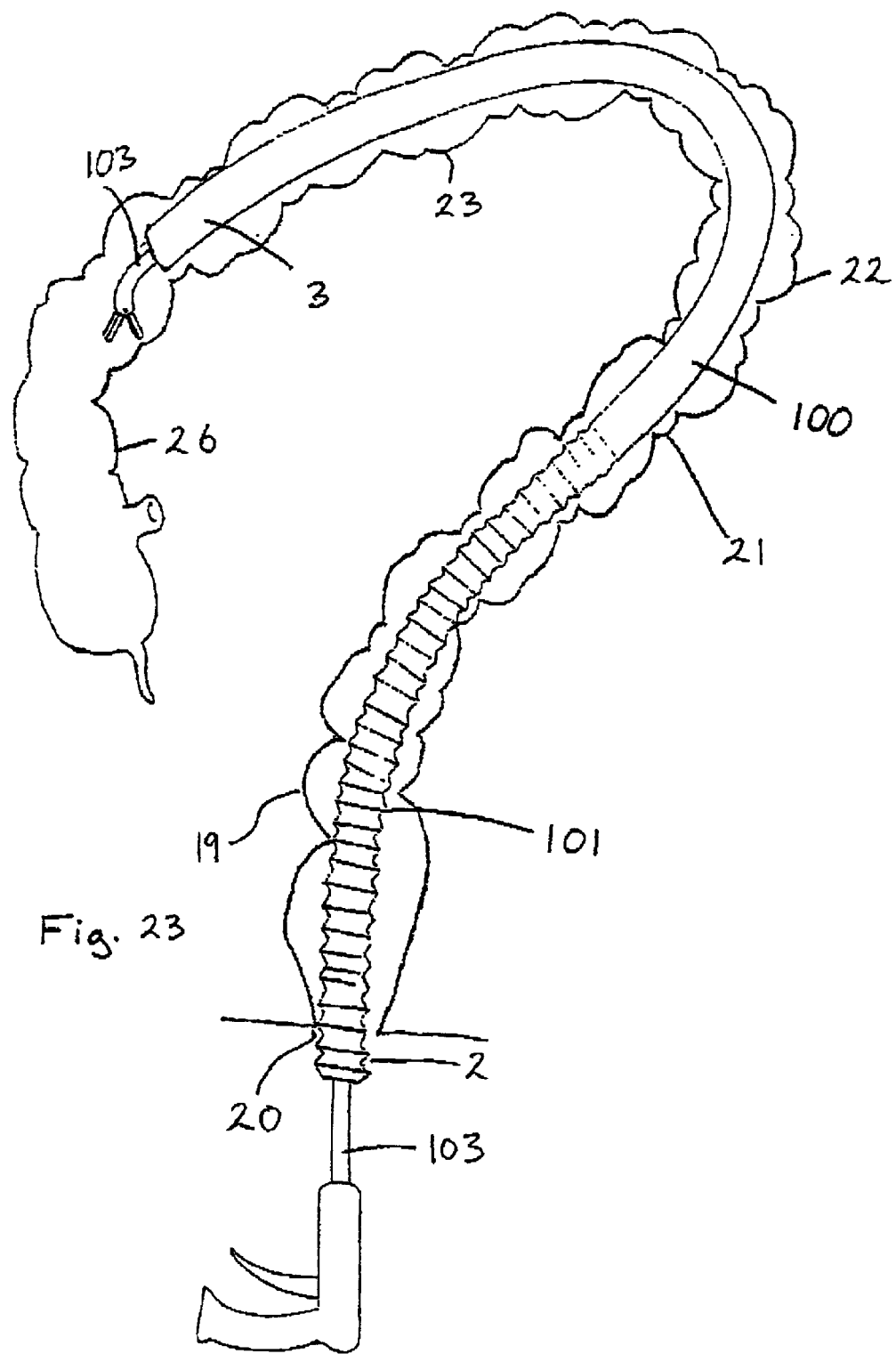

Referring to FIGS. 18 to 23, there is illustrated another colonic overtube 100 according to the insertion for cannulating a colon. The overtube 100 is similar to the overtube 1 of FIGS. 1 to 17, and similar elements in FIGS. 18 to 23 are assigned the same reference numerals. The overtube 100 is extendable between a shortened configuration, as illustrated in FIGS. 18 to 20, and an elongated configuration, as illustrated in FIGS. 21 to 23, for cannulating at least portion of the colon 18, in particular cannulating the colon 18 to a point distally of the descending colon 22. In this case, a portion 101 of the overtube 100 has a concertina-type configuration in the shortened configuration (FIG. 18), and a flattened out configuration in the elongated configuration (FIG. 21). The concertinaed portion 101 is provided at the proximal end 2 of the overtube 100.

In use, the overtube 100 is mounted to the colonoscope 14 with the portion 101 retracted into the concertina-like manner before insertion of the colonoscope 2 into the colon 18. Insertion of the colonoscope 14 into the colon 18, straightening of the sigmoid colon 21 and advancement of the overtube 100 over the colonoscope 14 are performed in a manner similar to that described previously with reference to FIGS. 12 to 17.

The overtube 100 acts as a splint to maintain the sigmoid colon 21 in the straightened configuration. The colonoscope 14 may therefore be easily advanced through the transverse colon 23 to the hepatic flexure 25 (FIG. 18). The transverse colon 23 is straightened in the normal manner as routinely performed by those skilled in the art (FIG. 19), and the colonoscope 4 is further advanced into the ascending colon 26 (FIG. 20).

The concertinaed portion 101 of the overtube 100 is then extended from the shortened configuration to the elongated configuration, by pushing the overtube 100 distally from externally of the colon 18. In this way the overtube 100 is advanced distally over the colonoscope 14 through the descending colon 22 and the transverse colon 23 until the distal end 3 of the overtube 100 reaches any desired point of interest in the colon 18 as far distally as the caecum (FIG. 21).

The overtube 100 of the invention acts as a colonic cannula and maintains in a straightened configuration the sections of the colon 18 that are normally mobile such as the sigmoid colon 21 and the transverse colon 23. This gives the colon 18 the classic question mark configuration as shown in FIG. 21. The colonoscope 14 may therefore be removed through the colonoscope lumen 4 from the colon 18 leaving the overtube 100 in place in the cannulated colon 18 (FIG. 22). The overtube 100 can then be used to facilitate insertion of an endoscopic instrument through the overtube 100, for example an instrument 103 to remove polyps from the ascending colon 26 (FIG. 23), or the overtube 100 can be used to facilitate reinsertion of a colonoscope.

If a subsequent region of interest in the colon 18 is proximally or distally of the distal end 3 of the overtube 100, the overtube 100 can be shortened or elongated until the distal end 3 is at the desired region of interest. While shortening or withdrawal of the overtube 100 may be achieved by simply withdrawing the overtube 100 from the colon 18, advancement or lengthening of the overtube 100 is preferably achieved with the colonoscope 14 in situ in the colon 18.

When the colonoscope 14 has been removed from the overtube 100, the overtube 100 provides a large working channel through the colon 18 through which any instrument may be quickly and easily passed to access any point in the colon 18 as far distally as the caecum. Rapid and less painful exchange of instruments and/or colonoscopes is thus facilitated by the overtube 100 because there is no contact between the instruments/colonoscopes and the inner wall of the colon 18 during insertion or withdrawal of the instruments/colonoscopes. In addition, the overtube 100 has a much larger diameter than the diameter of a typical colonoscope working channel. Thus, larger instruments may be used during a colonoscopy procedure with the overtube 100. Larger samples may also be removed using the overtube 100.

The overtube 100 is removed from the colon 18 by collapsing the elongated portion 101 to the shortened configuration and withdrawing the overtube 100 proximally out of the colon 18. It is not necessary to reintroduce the colonoscope 14 into the colon 18 to facilitate removal of the overtube 100. Alternatively the overtube 100 may be withdrawn from the colon 18 leaving the colonoscope 14 in place in the colon 18. In this case, the colonoscope 14 may be subsequently withdrawn from the colon 18 thereby enabling the entire colon 18 to be examined during withdrawal of the colonoscope 14.

It will be appreciated that the overtube may be extended in a number of alternative ways. For example, the overtube may comprise a plurality of overtube sections which are releasably mountable to one another to extend the overtube to the elongated configuration in a manner similar to the extension of a chimney sweeping brush, as a further possibility. As a further possibility the overtube may comprise one or more telescopable sections.

In an alternative arrangement, a connecting means, such as a drawstring, may be passed distally through the colonoscope working channel out of the distal end 15 of the colonoscope 14 and attached to the distal end 3 of the overtube 100. By maintaining the position of the colonoscope 14 fixed and pulling proximally on the connecting means from externally of the colon 18, the distal end 3 of the overtube 100 can be advanced over the colonoscope 2 thereby extending the concertinaed portion 101 of the overtube 100.

Other means of activating an actuator of the overtube from externally of the colon may also be applied to extend the overtube in situ to the elongated configuration. For example, the overtube may at least partially comprise an energy actuated polymer. By application of energy, such as a voltage difference across the overtube, a portion of the overtube may be extended.

The overtube 100 may have one or more laterally flexible portions spaced along the overtube 100, similar to the corrugated arrangement of FIG. 1, and/or the composite arrangement of FIG. 33. These laterally flexible portions may assist navigation of tight bends in the colon 18, such as the splenic and hepatic flexures.

Figure 24:
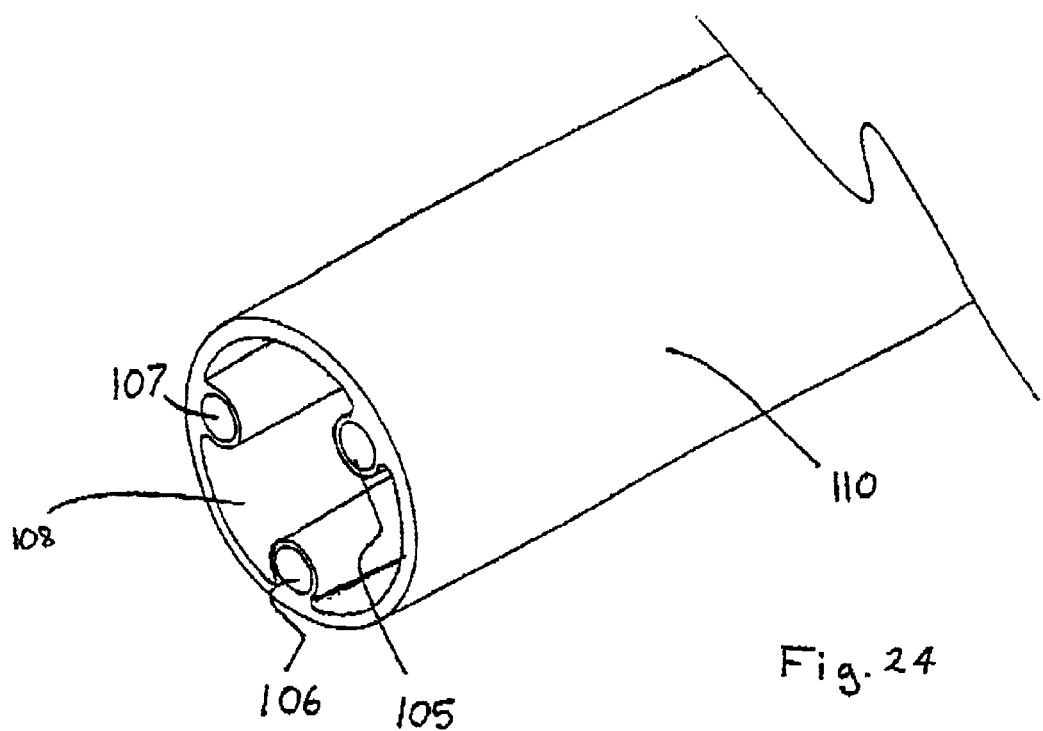
FIG. 24 is a perspective view of a distal end of a further colonic overtube according to the invention.

FIG. 24 illustrates another colonic overtube 110 according to the invention which is similar to the overtube 1 of FIGS. 1 to 17. The overtube 110 comprises at least one, and in this case three, exchange lumena 105, 106, 107, extending through the overtube 110 in addition to the colonoscope lumen 108. The exchange lumena 105, 106, 107 are suitable for exchanging a fluid, or a medical device through the lumena 105, 106, 107. For example, the lumen 105 may be used to provide a channel through which means for viewing the colon 18 from externally of the colon 18 can be provided, or the lumen 106 may be used to provide a channel through which means for illuminating the colon 18 can be provided.

It is highly advantageous to advance the overtube 100 with a visible path distally of the overtube 100 to ensure that no bowel is trapped at the distal end 3 of the overtube 100 during advancement through the colon 18.

As a further alternative, the lumen 107 may be used to provide a channel for flushing or insufflating the colon 18, for example to blow a protruding piece of the colon 18 laterally to clear a path for safe advancement of the overtube 100 through the colon 18.

In the case of the overtube 110 of FIG. 24, the exchange lumena 105, 106, 107 are provided on an interior surface of the overtube 110 extending inwardly into the colonoscope lumen 108. It will be appreciated that one or more of the exchange lumena may alternatively be provided on an exterior surface of the overtube 110 extending outwardly.

The colonoscope lumen 4 has a diameter, in this case approximately 15 mm, which results in a significantly larger cross sectional area than that of a typical colonoscope working channel.

To assist with and speed up advancement of the overtube of the invention into the colon 18 over the colonoscope 14 a guide device may be used, such as the guide device described in International Patent Application No. PCT/IE01/00039, the relevant contents of which are incorporated herein by reference.

The overtube of the invention may be applied to maintain sections of the colon other than the sigmoid colon in a straightened configuration. Indeed the overtube could also be applied to cannulate other body lumena, in which medical instruments are to be inserted.

The invention is not limited to the embodiments hereinbefore described, with reference to the accompanying drawings, which may be varied in construction and detail.

What is claimed is:

1. A colonic overtube for maintaining a section of a colon in a straightened configuration, the overtube having a proximal end for location externally of a colon, and a distal end for insertion into a colon, and a colonoscope lumen extending therethrough for passing the overtube over a colonoscope;
    the overtube comprising a flexible seal at the distal end for sealing between the overtube and a colonoscope extending through the colonoscope lumen;
    the seal being mounted to an exterior surface of the overtube, and the seal extending inwardly to seal between the overtube and a colonoscope extending through the colonoscope lumen.

2. An overtube as claimed in claim 1 wherein;
    at least portion of the overtube is laterally flexible to facilitate flexing of the overtube substantially without kinking during advancement of the overtube through a colon.

3. An overtube as claimed in claim 1 wherein the laterally flexible portion of the overtube extends along the entire length of the overtube.

4. An overtube as claimed in claim 1 wherein the overtube has more than one laterally flexible portion spaced along the overtube.

5. An overtube as claimed in claim 1 wherein the laterally flexible portion is provided by at least one corrugation.

6. An overtube as claimed in claim 5 wherein the corrugation extends along the overtube in a convoluted manner.

7. An overtube as claimed in claim 5 wherein the corrugation extends at least partially circumferentially around the overtube.

8. An overtube as claimed in claim 5 wherein the overtube comprises a plurality of corrugations.

9. An overtube as claimed in claim 5 wherein the corrugation is provided on an interior surface of the overtube.

10. An overtube as claimed in claim 1 wherein an exterior surface of the overtube is smooth.

11. An overtube as claimed in claim 1 wherein the overtube comprises a coating of a lubricious material.

12. An overtube as claimed in claim 1 wherein the overtube comprises a composite material.

13. An overtube as claimed in claim 12 wherein the overtube is of a layered construction.

14. An overtube as claimed in claim 12 wherein the overtube comprises a reinforcement means element.

15. An overtube as claimed in claim 14 wherein the reinforcement means element is embedded in the overtube.

16. An overtube as claimed in claim 14 wherein the reinforcement means element comprises a coil.

17. An overtube as claimed in claim 14 wherein the reinforcement means element comprises a mesh.

18. An overtube as claimed in claim 14 wherein the reinforcement element is of a braided construction.

19. An overtube as claimed in claim 14 wherein the reinforcement element is of a metallic material.

20. An overtube as claimed in claim 1 wherein the seal comprises a film material.

21. An overtube as claimed in claim 20 wherein the seal comprises a sheath of film material.

22. An overtube as claimed in claim 1 wherein the seal comprises an inner sealing layer and an outer sealing layer around the inner sealing layer.

23. An overtube as claimed in claim 1 wherein the seal extends distally of the distal end of the overtube.

24. An overtube as claimed in claim 1 wherein the overtube is of a material which is thermally stable in use.

25. An overtube as claimed in claim 24 wherein the overtube is of polytetrafluoroethylene.

26. An overtube as claimed in claim 1 wherein the overtube is extendable between a shortened configuration and an elongated configuration for cannulating at least portion of a colon.

27. An overtube as claimed in claim 26 wherein in the shortened configuration at least portion of the overtube is retracted in a concertina-like manner.

28. An overtube as claimed in claim 26 wherein the overtube comprises a plurality of overtube sections which are movable relative to one another to extend the overtube to the elongated configuration.

29. An overtube as claimed in claim 26 wherein the overtube comprises an actuator to extend the overtube in situ to the elongated configuration.

30. An overtube as claimed in claim 29 wherein the actuator may be activated from externally of a colon.

31. An overtube as claimed in claim 30 wherein the actuator comprises a connector for extending from the overtube within a colon to a location externally of the colon.

32. An overtube as claimed in claim 31 wherein the connector extends from the distal end of the overtube.

33. An overtube as claimed in claim 31 wherein the connector is anchored to the overtube.

34. An overtube as claimed in claim 31 wherein the connector comprises a drawstring.

35. An overtube as claimed in claim 34 wherein the drawstring is configured to be looped through a working channel of a colonoscope to a location externally of a colonoscope.

36. An overtube as claimed in claim 1 wherein the overtube comprises a rounded tip at the distal end for atraumatic advancement of the overtube through a colon.

37. An overtube as claimed in claim 36 wherein the tip is mounted to the overtube.

38. An overtube as claimed in claim 37 wherein the tip is mounted to an exterior surface of the overtube.

39. An overtube as claimed in claim 38 wherein the tip extends around the distal end of the overtube at least partially into the colonoscope lumen.

40. An overtube as claimed in claim 1 wherein the overtube comprises at least one exchange lumen for exchange of fluid and/or a medical device through the lumen.

41. An overtube as claimed in claim 40 wherein the overtube comprises means to view a colon distally of the overtube, the viewing means being at least partially provided in the exchange lumen.

42. An overtube as claimed in claim 40 wherein the overtube comprises means to insufflate a colon, the exchange lumen providing an insufflation channel.

43. An overtube as claimed in claim 40 wherein the overtube comprises means to flush a colon, the exchange lumen providing a flushing channel.

44. An overtube as claimed in claim 40 wherein the overtube comprises means to illuminate a colon, the illumination means being at least partially provided in the exchange lumen.

45. An overtube as claimed in claim 1 wherein the overtube comprises a limiting element to prevent complete insertion of the overtube into a colon.

46. An overtube as claimed in claim 45 wherein the position of the limiting element on the overtube is adjustable.

47. An overtube as claimed in claim 45 wherein the limiting element is releasably mounted to the overtube.

48. An overtube as claimed in claim 47 wherein the limiting element is threadably mounted to the overtube.

49. An overtube as claimed in claim 45 wherein the limiting element comprises a flange.

50. An overtube as claimed in claim 1 wherein the overtube has a discontinuous interior surface for ease of passage of the overtube over a colonoscope.

51. An overtube as claimed in claim 50 wherein the overtube comprises one or more inwardly projecting elements on the interior surface for contacting a colonoscope.

52. An overtube as claimed in claim 51 wherein the projecting element comprises a corrugation.

53. An overtube as claimed in claim 52 wherein the projecting element extends longitudinally along the overtube.

54. An overtube as claimed in claim 52 wherein the projecting element extends at least partially circumferentially around the overtube.

55. An overtube as claimed in claim 52 wherein the projecting element extends along the overtube in a convoluted manner.

56. An overtube as claimed in claim 51 wherein the projecting element comprises a protruding strip.

57. An overtube as claimed in claim 51 wherein the projecting element comprises a plurality of discrete protrusions.

58. A method of performing a colonoscopy procedure, the method comprising the steps of:
   inserting a colonoscope into a colon and advancing the colonoscope through at least part of the colon;
   straightening a section of the colon;
   advancing a colonic overtube over the colonoscope to maintain the section of the colon in a straightened configuration;
   advancing the colonoscope to a point distally of the straightened section of colon; and
   advancing the overtube over the colonoscope to a point distally of the straightened section of colon by extending the overtube from a shortened configuration to an elongated configuration.

59. A method as claimed in claim 58 wherein the method comprises the step of withdrawing the colonoscope from the colon while the overtube remains in place in the colon.

60. A method as claimed in claim 59 wherein the method comprises the step of advancing a medical device through the overtube to access a point in the colon distally of the straightened section of colon.

61. A method as claimed in claim 58 wherein the method comprises the step of mounting the overtube to the colonoscope before inserting the colonoscope into the colon.

62. A method as claimed in claim 58 wherein the overtube is advanced by pushing the overtube from externally of the colon.

63. A method as claimed in claim 58 wherein the section of colon being straightened is the sigmoid colon.

64. A method as claimed in claim 58 wherein the overtube is advanced to a point distally of the descending colon.

65. A colonic overtube for maintaining a section of a colon in a straightened configuration, the overtube having a proximal end for location externally of a colon, and a distal end for insertion into a colon, and a colonoscope lumen extending therethrough for passing the overtube over a colonoscope;
   the overtube comprising a flexible seal at the distal end for sealing between the overtube and a colonoscope extending through the colonoscope lumen;
   the seal comprising an inner sealing layer and an outer sealing layer around the inner sealing layer.

66. A colonic overtube having a proximal end for location externally of a colon, a distal end for insertion into a colon, and a colonoscope lumen extending therethrough for passing the overtube over a colonoscope:
   the overtube being extendable between a shortened configuration and an elongated configuration for cannulating at least portion of a colon;
   the overtube comprising an actuator to extend the overtube in situ to the elongated configuration;
   the actuator being activatable from externally of a colon;
   the actuator comprising a connector for extending from the overtube within a colon to a location externally of the colon;
   the connector comprising a drawstring.

67. An overtube as claimed in claim 66 wherein in the shortened configuration at least portion of the overtube is retracted in a concertina-like manner.

68. An overtube as claimed in claim 66 wherein the overtube comprises a plurality of overtube sections which are movable relative to one another to extend the overtube to the elongated configuration.

69. An overtube as claimed in claim 66 wherein the connector extends from the distal end of the overtube.

70. An overtube as claimed in claim 66 wherein the connector is anchored to the overtube.

71. An overtube as claimed in claim 66 wherein the drawstring is configured to be looped through a working channel of a colonoscope to a location externally of a colonoscope.

* * * * *